US010950019B2

(12) United States Patent
Akahori et al.

(10) Patent No.: US 10,950,019 B2
(45) Date of Patent: Mar. 16, 2021

(54) AUTOMATIC LAYOUT APPARATUS, AUTOMATIC LAYOUT METHOD, AND AUTOMATIC LAYOUT PROGRAM

(71) Applicants: FUJIFILM Corporation, Tokyo (JP); FUJIFILM Medical Systems USA Inc., Stamford, CT (US)

(72) Inventors: Sadato Akahori, Tokyo (JP); Keiji Sugihara, Morrisville, NC (US)

(73) Assignees: FUJIFILM Corporation, Tokyo (JP); FUJIFILM MEDICAL SYSTEMS USA INC, Stamford, CT (US)

(*) Notice: Subject to any disclaimer, the term of this patent is extended or adjusted under 35 U.S.C. 154(b) by 19 days.

(21) Appl. No.: 15/948,212

(22) Filed: Apr. 9, 2018

(65) Prior Publication Data
US 2018/0293772 A1 Oct. 11, 2018

Related U.S. Application Data
(60) Provisional application No. 62/483,492, filed on Apr. 10, 2017.

(51) Int. Cl.
G06T 11/60 (2006.01)
G06T 7/73 (2017.01)
(Continued)

(52) U.S. Cl.
CPC ............ G06T 11/60 (2013.01); A61B 5/7425 (2013.01); G06T 7/74 (2017.01); G06T 7/97 (2017.01);
(Continued)

(58) Field of Classification Search
CPC . G06T 2207/10072; G06T 2207/10076; G06T 2207/10081; G06T 2207/10084;
(Continued)

(56) References Cited

U.S. PATENT DOCUMENTS 6,072,903 A * 6/2000 Maki ................. G06T 7/246
348/169
6,500,118 B1 * 12/2002 Hashimoto .............. A61B 8/00
128/916
(Continued)

FOREIGN PATENT DOCUMENTS

JP 2001-137230 A 5/2001
JP 2004-160103 A 6/2004
(Continued)

OTHER PUBLICATIONS

Torresani et al., "Feature Correspondence via Graph Matching: Models and Global Optimization", European Conference on Computer Vision, 2008, 14 pages.
(Continued)

Primary Examiner — Charles L Beard
(74) Attorney, Agent, or Firm — Birch, Stewart, Kolasch & Birch, LLP

(57) ABSTRACT

Reception means receives examination data including a plurality of examination images. Association means associates an examination image similar to each sample image included in the layout with a sample image using a similarity between each sample image included in a layout and each of a plurality of examination images included in examination data. Display means displays the examination image associated with the sample image at an arrangement position where the sample image is arranged in the layout.

10 Claims, 12 Drawing Sheets

(51) Int. Cl.
*G06T 7/00* (2017.01)
*A61B 5/00* (2006.01)

(52) U.S. Cl.
CPC ............ *G06T 2207/10072* (2013.01); *G06T 2207/20072* (2013.01); *G06T 2207/20212* (2013.01); *G06T 2210/41* (2013.01)

(58) Field of Classification Search
CPC . G06T 2207/10088; G06T 2207/10092; G06T 2207/10096; G06T 2207/10101; G06T 2207/10104; G06T 2207/10108; G06T 2207/10112; G06T 2207/10116; G06T 11/60; G06T 7/74; G06T 7/97; G06T 2207/20072; G06T 2207/20212; G06T 2210/41; A61B 5/7425
See application file for complete search history.

(56) References Cited

U.S. PATENT DOCUMENTS

| | | | | |
|---|---|---|---|---|
| 6,901,277 | B2* | 5/2005 | Kaufman | A61B 5/411 128/922 |
| 6,928,314 | B1* | 8/2005 | Johnson | G06T 15/08 128/920 |
| 7,130,457 | B2* | 10/2006 | Kaufman | G06F 19/321 382/128 |
| 7,570,791 | B2* | 8/2009 | Frank | A61B 6/4441 382/128 |
| 7,880,936 | B2* | 2/2011 | Shiiyama | G11B 27/031 358/452 |
| 7,949,166 | B2* | 5/2011 | Moriya | G06F 19/321 382/128 |
| 8,094,901 | B1* | 1/2012 | Reicher | G06F 19/321 382/128 |
| 8,160,676 | B2* | 4/2012 | Gielen | A61B 5/06 382/128 |
| 8,166,391 | B2* | 4/2012 | Kaneko | G06T 11/60 715/247 |
| 8,189,883 | B2* | 5/2012 | Oosawa | G16H 30/20 382/128 |
| 8,923,580 | B2* | 12/2014 | Dekel | G06F 19/321 382/128 |
| 8,958,613 | B2* | 2/2015 | Kondo | G16H 50/70 382/128 |
| 8,976,190 | B1* | 3/2015 | Westerhoff | G06F 19/321 345/581 |
| 9,008,390 | B2* | 4/2015 | Takata | G06F 19/00 382/128 |
| 9,015,579 | B2* | 4/2015 | Jin | H04N 1/00132 715/243 |
| 9,152,760 | B2* | 10/2015 | Sherman | G06F 19/321 |
| 9,189,569 | B2* | 11/2015 | Abe | G06F 19/32 |
| 9,235,575 | B1* | 1/2016 | Xiao | G06F 16/4393 |
| 9,254,098 | B2* | 2/2016 | Charles | A61B 5/055 |
| 9,325,869 | B2* | 4/2016 | Nagasaka | H04N 1/0045 |
| 9,690,902 | B2* | 6/2017 | Arakita | G06F 19/321 |
| 9,875,256 | B2* | 1/2018 | Takata | G16H 50/70 |
| 10,026,009 | B2* | 7/2018 | Yang | H04N 1/6027 |
| 10,055,543 | B2* | 8/2018 | Kozuka | G06T 19/00 |
| 10,185,893 | B2* | 1/2019 | Townsend | G06K 9/6261 |
| 10,304,564 | B1* | 5/2019 | Reicher | G16H 30/20 |
| 10,331,851 | B2* | 6/2019 | Takata | G06F 19/321 |
| 10,380,740 | B2* | 8/2019 | Canda | G16H 30/40 |
| 10,405,811 | B2* | 9/2019 | Haque | G01N 15/1475 |
| 10,803,986 | B2* | 10/2020 | Nakamura | A61B 8/565 |
| 2002/0030634 | A1* | 3/2002 | Noda | H04N 1/387 345/5 |
| 2002/0103429 | A1* | 8/2002 | deCharms | A61B 5/055 600/410 |
| 2003/0018245 | A1* | 1/2003 | Kaufman | A61B 5/411 600/407 |
| 2004/0013302 | A1* | 1/2004 | Ma | G06F 16/83 382/209 |
| 2004/0109008 | A1* | 6/2004 | Sako | G06T 7/0012 345/629 |
| 2004/0213444 | A1* | 10/2004 | Yamamichi | G06T 19/00 382/128 |
| 2005/0129325 | A1* | 6/2005 | Wu | H04N 7/144 382/254 |
| 2005/0152588 | A1* | 7/2005 | Yoshida | G06T 7/0012 382/128 |
| 2005/0203385 | A1 | 9/2005 | Sundar et al. | |
| 2005/0207630 | A1* | 9/2005 | Chan | A61B 6/466 382/131 |
| 2006/0279555 | A1* | 12/2006 | Ono | G06T 11/60 345/173 |
| 2007/0204209 | A1* | 8/2007 | Truelove | G06F 16/4393 715/203 |
| 2008/0008401 | A1* | 1/2008 | Zhu | G06F 19/321 382/294 |
| 2008/0019581 | A1* | 1/2008 | Gkanatsios | A61B 6/025 382/131 |
| 2008/0100709 | A1* | 5/2008 | Furukawa | G06T 7/12 348/169 |
| 2008/0123927 | A1* | 5/2008 | Miga | G06T 7/344 382/131 |
| 2008/0221441 | A1* | 9/2008 | Bjornerud | G06T 7/0012 600/425 |
| 2008/0260226 | A1* | 10/2008 | Moriya | G06K 9/6201 382/128 |
| 2008/0266582 | A1* | 10/2008 | Sakura | G06F 3/1208 358/1.6 |
| 2008/0292169 | A1* | 11/2008 | Wang | G06T 7/0012 382/131 |
| 2009/0002764 | A1* | 1/2009 | Atkins | G06T 11/60 358/1.18 |
| 2009/0003702 | A1* | 1/2009 | Ofek | G06T 11/001 382/181 |
| 2009/0082660 | A1* | 3/2009 | Rahn | A61B 6/12 600/411 |
| 2009/0116752 | A1* | 5/2009 | Isomura | G06T 11/60 382/217 |
| 2009/0169132 | A1* | 7/2009 | Sagawa | G06T 11/60 382/295 |
| 2009/0213034 | A1* | 8/2009 | Wu | G06F 19/321 345/1.1 |
| 2009/0220135 | A1 | 9/2009 | Nakamura | |
| 2009/0226097 | A1* | 9/2009 | Matsumoto | G06T 3/403 382/199 |
| 2009/0268943 | A1* | 10/2009 | Yoshizumi | H04N 5/23222 382/103 |
| 2009/0304272 | A1* | 12/2009 | Makadia | G06K 9/00664 382/165 |
| 2010/0104167 | A1* | 4/2010 | Sakaguchi | G06T 7/11 382/132 |
| 2010/0106002 | A1* | 4/2010 | Sugiyama | A61B 5/055 600/410 |
| 2010/0111396 | A1* | 5/2010 | Boucheron | G06K 9/0014 382/133 |
| 2010/0113091 | A1* | 5/2010 | Sharma | G06K 9/4642 455/556.1 |
| 2010/0128841 | A1* | 5/2010 | Imas | G06T 5/002 378/16 |
| 2010/0131890 | A1* | 5/2010 | Natanzon | G06F 3/0481 715/808 |
| 2010/0135562 | A1* | 6/2010 | Greenberg | G06F 19/321 382/131 |
| 2010/0157155 | A1* | 6/2010 | Katsushima | A61B 6/463 348/564 |
| 2010/0157352 | A1* | 6/2010 | Morales | G06F 3/04845 358/1.15 |
| 2010/0160765 | A1* | 6/2010 | Marrouche | G06T 7/0012 600/410 |
| 2010/0164992 | A1* | 7/2010 | Akiya | H04N 1/00456 345/641 |
| 2010/0188519 | A1* | 7/2010 | Yamaoka | G06K 9/00369 348/222.1 |
| 2010/0199227 | A1* | 8/2010 | Xiao | G06F 3/0481 715/863 |

(56) References Cited

U.S. PATENT DOCUMENTS

| | | | |
|---|---|---|---|
| 2010/0232661 A1* | 9/2010 | Hisanaga | G16H 30/40 382/128 |
| 2010/0259650 A1* | 10/2010 | Sasaki | G06K 9/6212 348/241 |
| 2010/0278405 A1* | 11/2010 | Kakadiaris | G16H 50/30 382/131 |
| 2010/0290671 A1* | 11/2010 | Shimizu | G06K 9/00771 382/103 |
| 2010/0290679 A1* | 11/2010 | Gasser | G06T 17/20 382/128 |
| 2011/0002549 A1* | 1/2011 | Ohmori | G06K 9/6203 382/218 |
| 2011/0075950 A1* | 3/2011 | Ohashi | G06K 9/4642 382/305 |
| 2011/0188722 A1* | 8/2011 | Huang | G01R 33/56 382/131 |
| 2011/0222766 A1* | 9/2011 | Kato | G06K 9/481 382/168 |
| 2011/0234613 A1* | 9/2011 | Hanson | G06F 16/58 345/589 |
| 2011/0235066 A1* | 9/2011 | Sakuragi | H04N 13/361 358/1.6 |
| 2011/0235884 A1* | 9/2011 | Schreibmann | G06T 7/30 382/131 |
| 2011/0243401 A1* | 10/2011 | Zabair | G06K 9/00 382/128 |
| 2011/0280456 A1* | 11/2011 | Sussman | G01R 33/5608 382/131 |
| 2011/0305377 A1* | 12/2011 | Drozdzal | A61B 1/00009 382/128 |
| 2011/0310964 A1* | 12/2011 | Beymer | G06T 3/4053 375/240.08 |
| 2012/0008734 A1* | 1/2012 | Thomson | G06T 7/0014 378/4 |
| 2012/0035963 A1* | 2/2012 | Qian | G16H 15/00 705/3 |
| 2012/0063655 A1* | 3/2012 | Dean | G16H 50/50 382/128 |
| 2012/0070040 A1* | 3/2012 | Vans | B41F 33/0036 382/112 |
| 2012/0078045 A1* | 3/2012 | Sasaki | A61B 1/00009 600/109 |
| 2012/0092617 A1* | 4/2012 | Muto | A61B 3/102 351/206 |
| 2012/0098994 A1* | 4/2012 | Cheatle | G11B 27/034 348/222.1 |
| 2012/0106794 A1* | 5/2012 | Iwasaki | G06T 7/215 382/103 |
| 2012/0120217 A1* | 5/2012 | Sasaki | A61B 1/00006 348/65 |
| 2012/0131498 A1* | 5/2012 | Gross | G06F 16/54 715/788 |
| 2012/0154608 A1* | 6/2012 | Ko | G11B 27/34 348/207.11 |
| 2012/0189176 A1* | 7/2012 | Giger | G06T 7/0016 382/128 |
| 2012/0206496 A1* | 8/2012 | Cok | G06Q 10/00 345/672 |
| 2012/0207396 A1* | 8/2012 | Dong | G06T 5/002 382/218 |
| 2012/0218290 A1* | 8/2012 | Waschbuesch | G09G 5/377 345/619 |
| 2012/0230566 A1* | 9/2012 | Dean | A61B 34/10 382/131 |
| 2012/0275713 A1* | 11/2012 | Yamanakajima | H04N 1/32128 382/218 |
| 2012/0287131 A1* | 11/2012 | Matsuzaki | A61B 6/025 345/426 |
| 2012/0321166 A1* | 12/2012 | Kitamura | A61B 3/0058 382/131 |
| 2012/0328190 A1* | 12/2012 | Bercovich | G06F 16/5866 382/165 |
| 2013/0004073 A1* | 1/2013 | Yamaji | G06T 11/60 382/173 |
| 2013/0028516 A1* | 1/2013 | Warfield | G06T 1/00 382/173 |
| 2013/0028521 A1* | 1/2013 | Yabu | G06T 11/60 382/195 |
| 2013/0125002 A1* | 5/2013 | Spaeth | G06F 3/0482 715/731 |
| 2013/0129165 A1 | 5/2013 | Dekel et al. | |
| 2013/0129198 A1* | 5/2013 | Sherman | G16H 30/20 382/159 |
| 2013/0195359 A1* | 8/2013 | Yabu | H04N 1/3876 382/171 |
| 2013/0211238 A1* | 8/2013 | DeCharms | A61B 5/4824 600/418 |
| 2013/0296701 A1* | 11/2013 | Zalev | A61B 5/0095 600/440 |
| 2013/0308867 A1* | 11/2013 | Baba | G06K 9/46 382/195 |
| 2013/0324849 A1* | 12/2013 | Park | A61B 8/463 600/440 |
| 2014/0003695 A1* | 1/2014 | Dean | G06T 7/0012 382/131 |
| 2014/0009495 A1* | 1/2014 | Sakai | G06T 11/60 345/634 |
| 2014/0010451 A1* | 1/2014 | Sumi | G06T 11/60 382/173 |
| 2014/0010459 A1* | 1/2014 | Sumi | G06K 9/00221 382/195 |
| 2014/0010463 A1* | 1/2014 | Kato | G06K 9/6202 382/218 |
| 2014/0010464 A1* | 1/2014 | Umeda | G06T 11/60 382/224 |
| 2014/0010477 A1* | 1/2014 | Kotani | H04N 1/3935 382/298 |
| 2014/0093150 A1* | 4/2014 | Zalev | G06T 7/0012 382/131 |
| 2014/0118544 A1* | 5/2014 | Asaka | G06T 7/0002 348/143 |
| 2014/0143710 A1* | 5/2014 | Zhao | G06F 19/321 715/781 |
| 2014/0172458 A1* | 6/2014 | Ueda | G06F 19/321 705/3 |
| 2014/0376822 A1* | 12/2014 | Holroyd | G06T 7/246 382/219 |
| 2015/0036924 A1* | 2/2015 | Kuusisto | G06K 9/4638 382/165 |
| 2015/0055846 A1* | 2/2015 | Haque | A61B 5/7425 382/131 |
| 2015/0091778 A1* | 4/2015 | Day | G16H 30/40 345/1.3 |
| 2015/0093005 A1* | 4/2015 | Oh | A61B 6/466 382/131 |
| 2015/0154356 A1* | 6/2015 | Alvarez Del Castillo | G06F 19/321 715/853 |
| 2015/0169207 A1* | 6/2015 | Mody | G06F 9/451 715/763 |
| 2015/0178786 A1* | 6/2015 | Claessens | G06Q 30/0269 705/14.66 |
| 2015/0223901 A1* | 8/2015 | Wei | G06F 19/321 703/11 |
| 2015/0243045 A1* | 8/2015 | Ra | A61B 6/032 382/131 |
| 2015/0248429 A1* | 9/2015 | Pregueiro | G06F 16/168 715/202 |
| 2015/0269456 A1* | 9/2015 | Yang | G06K 9/6215 382/219 |
| 2015/0278595 A1* | 10/2015 | Momoki | G06F 16/51 382/218 |
| 2015/0287194 A1* | 10/2015 | Schoenmeyer | G06T 7/0012 382/128 |
| 2015/0288869 A1* | 10/2015 | Furuhashi | H04N 5/76 348/207.11 |
| 2015/0317434 A1* | 11/2015 | Kondo | A61B 5/00 705/3 |

(56) References Cited

U.S. PATENT DOCUMENTS

| | | | |
|---|---|---|---|
| 2015/0317452 A1* | 11/2015 | Kozuka | G16H 15/00 705/2 |
| 2015/0324536 A1* | 11/2015 | Shie | G06Q 50/24 715/753 |
| 2015/0324993 A1* | 11/2015 | Stein | G06T 7/10 382/164 |
| 2015/0339822 A1* | 11/2015 | Onda | G06T 1/0007 382/128 |
| 2015/0347464 A1* | 12/2015 | Takata | G06F 19/321 707/728 |
| 2015/0347505 A1* | 12/2015 | Ohashi | G06Q 50/24 707/754 |
| 2015/0348261 A1* | 12/2015 | Sunami | A61B 6/032 382/131 |
| 2015/0356271 A1* | 12/2015 | Kozuka | G06F 16/5838 705/2 |
| 2015/0363053 A1* | 12/2015 | Aoyama | G06F 3/0482 715/838 |
| 2015/0371381 A1* | 12/2015 | Sato | G06T 7/0012 382/132 |
| 2016/0005158 A1* | 1/2016 | Asano | G06T 11/60 382/154 |
| 2016/0006936 A1* | 1/2016 | Hattori | G06T 5/50 382/166 |
| 2016/0015333 A1* | 1/2016 | Morita | A61B 6/502 378/22 |
| 2016/0019433 A1* | 1/2016 | Saito | G06F 16/5866 709/203 |
| 2016/0070436 A1* | 3/2016 | Thomas | A61B 5/055 715/771 |
| 2016/0071273 A1* | 3/2016 | Kim | G06K 9/4671 382/100 |
| 2016/0125162 A1* | 5/2016 | Takata | G06F 19/321 705/2 |
| 2016/0139761 A1* | 5/2016 | Grosz | H04N 1/00188 715/769 |
| 2016/0155229 A1* | 6/2016 | Shinoda | A61B 5/743 382/131 |
| 2016/0247300 A1* | 8/2016 | Takata | G06F 16/5854 |
| 2016/0253824 A1* | 9/2016 | Yu | H04N 5/222 348/46 |
| 2016/0275370 A1* | 9/2016 | Yang | G06K 9/6215 |
| 2016/0275685 A1* | 9/2016 | Nakagomi | G06T 7/0016 |
| 2016/0292844 A1* | 10/2016 | Karube | G06T 7/35 |
| 2016/0295036 A1* | 10/2016 | Momoki | H04N 1/00196 |
| 2016/0300120 A1* | 10/2016 | Haas | G06K 9/621 |
| 2016/0335332 A1* | 11/2016 | Pimento | G06F 16/17 |
| 2016/0345925 A1* | 12/2016 | Westerhoff | A61B 6/032 |
| 2017/0024852 A1* | 1/2017 | Oztireli | G06T 3/40 |
| 2017/0039670 A1* | 2/2017 | Obayashi | G06F 3/0481 |
| 2017/0039746 A1* | 2/2017 | Mizoguchi | G06K 9/00268 |
| 2017/0039747 A1* | 2/2017 | Ishida | G06T 11/60 |
| 2017/0039748 A1* | 2/2017 | Kunieda | G06T 11/60 |
| 2017/0061612 A1* | 3/2017 | Mizobe | G06T 5/50 |
| 2017/0090739 A1* | 3/2017 | Kozuka | G16H 30/20 |
| 2017/0091582 A1* | 3/2017 | Takata | A61B 5/055 |
| 2017/0119472 A1* | 5/2017 | Herrmann | A61B 34/10 |
| 2017/0127936 A1* | 5/2017 | Iwase | A61B 3/1225 |
| 2017/0186192 A1* | 6/2017 | Yang | G06T 11/003 |
| 2017/0193681 A1* | 7/2017 | Nomoto | G06K 9/00228 |
| 2017/0249534 A1* | 8/2017 | Townsend | G06K 9/6261 |
| 2017/0249767 A1* | 8/2017 | Fuss | G06T 11/60 |
| 2017/0273641 A1* | 9/2017 | Haque | A61B 6/03 |
| 2017/0358103 A1* | 12/2017 | Shao | G01S 3/00 |
| 2017/0365032 A1* | 12/2017 | Westerhoff | G06T 15/005 |
| 2017/0365075 A1* | 12/2017 | Meganck | G06T 7/0012 |
| 2017/0367685 A1* | 12/2017 | Zou | G06K 9/6215 |
| 2018/0018512 A1* | 1/2018 | Wang | G06K 9/00483 |
| 2018/0028079 A1* | 2/2018 | Gurevich | G06K 9/6219 |
| 2018/0070917 A1* | 3/2018 | Rothberg | A61B 8/12 |
| 2018/0084970 A1* | 3/2018 | Harada | A61B 1/00009 |
| 2018/0101645 A1* | 4/2018 | Sorenson | G06K 9/66 |
| 2018/0137244 A1* | 5/2018 | Sorenson | G06F 19/321 |
| 2018/0144458 A1* | 5/2018 | Xu | H04N 13/239 |
| 2018/0150433 A1* | 5/2018 | Sowden | G06T 1/0007 |
| 2018/0150954 A1* | 5/2018 | Nakagomi | G06T 7/0016 |
| 2018/0166167 A1* | 6/2018 | Kanada | G16H 30/20 |
| 2018/0184987 A1* | 7/2018 | Ishihara | A61B 5/05 |
| 2018/0197726 A1* | 7/2018 | Yamaguchi | G01N 27/62 |
| 2018/0232603 A1* | 8/2018 | Shim | A61B 6/00 |
| 2018/0260998 A1* | 9/2018 | Ohishi | G06T 15/08 |
| 2018/0268547 A1* | 9/2018 | Miyasa | G06T 7/97 |
| 2018/0285676 A1* | 10/2018 | Han | G06K 9/3258 |
| 2018/0288438 A1* | 10/2018 | Chao | H04N 19/147 |
| 2018/0293773 A1* | 10/2018 | Kohle | A61B 6/463 |
| 2018/0300885 A1* | 10/2018 | On | G06T 7/74 |
| 2018/0300889 A1* | 10/2018 | Tanaka | G06T 7/33 |
| 2018/0301216 A1* | 10/2018 | Nakamura | A61B 5/7425 |
| 2018/0307940 A1* | 10/2018 | Wang | G06K 9/6255 |
| 2018/0308244 A1* | 10/2018 | Akahori | G06K 9/469 |
| 2018/0330474 A1* | 11/2018 | Mehta | G06T 3/4076 |
| 2018/0349724 A1* | 12/2018 | Xiang | G06K 9/3233 |
| 2019/0012820 A1* | 1/2019 | Furuya | H04N 1/00196 |
| 2019/0066296 A1* | 2/2019 | Lee | A61B 8/5223 |
| 2019/0087939 A1* | 3/2019 | Hakimuddin | G06T 7/11 |
| 2019/0087971 A1* | 3/2019 | Sano | G06T 7/593 |
| 2019/0102516 A1* | 4/2019 | Schieke | G06T 7/143 |
| 2019/0102900 A1* | 4/2019 | Uchida | H04N 13/239 |
| 2019/0102926 A1* | 4/2019 | Obayashi | G06F 3/0481 |
| 2019/0131012 A1* | 5/2019 | Osawa | G06T 7/0012 |
| 2019/0139223 A1* | 5/2019 | Nie | G06K 9/3233 |
| 2019/0148015 A1* | 5/2019 | Futamura | G16H 30/40 705/2 |
| 2019/0156526 A1* | 5/2019 | Liu | G06T 11/008 |
| 2019/0172205 A1* | 6/2019 | Mao | G06T 7/149 |
| 2019/0179420 A1* | 6/2019 | Yamaoka | H04N 5/2224 |
| 2019/0189269 A1* | 6/2019 | Kato | G16H 30/40 |
| 2019/0208173 A1* | 7/2019 | Kadu | G06T 5/009 |
| 2019/0231296 A1* | 8/2019 | Jackson | A61B 6/542 |
| 2019/0262094 A1* | 8/2019 | Zhao | A61B 6/00 |
| 2019/0279384 A1* | 9/2019 | Sano | G06T 7/593 |
| 2019/0287245 A1* | 9/2019 | Shiroishi | G06T 7/11 |
| 2019/0306339 A1* | 10/2019 | Nishida | H04N 1/2323 |
| 2019/0320113 A1* | 10/2019 | Rajvanshi | H04N 5/23222 |
| 2019/0320205 A1* | 10/2019 | Lin | H04N 19/543 |
| 2019/0325621 A1* | 10/2019 | Wang | A61B 6/032 |
| 2019/0327367 A1* | 10/2019 | Obayashi | H04N 1/00167 |
| 2019/0378241 A1* | 12/2019 | Kabus | G06T 19/20 |
| 2019/0388182 A1* | 12/2019 | Kumar | G06T 7/337 |
| 2019/0392942 A1* | 12/2019 | Sorenson | G06T 7/11 |
| 2019/0392943 A1* | 12/2019 | Sorenson | G16H 30/20 |
| 2020/0075154 A1* | 3/2020 | Akahori | G16H 50/20 |
| 2020/0311454 A1* | 10/2020 | Horiike | G06K 9/2081 |

FOREIGN PATENT DOCUMENTS

| | | |
|---|---|---|
| JP | 2007-520280 A | 7/2007 |
| JP | 2007-260061 A | 10/2007 |
| JP | 2013-106951 A | 10/2007 |
| JP | 2007-286945 A | 11/2007 |
| JP | 2009-230755 A | 10/2009 |
| JP | 2010-211749 A | 9/2010 |
| JP | 2011-143159 A | 7/2011 |
| JP | 2011-1143159 A | 7/2011 |
| JP | 2011-239812 A | 12/2011 |
| JP | 2016-101439 A | 6/2016 |
| JP | 2016-171961 A | 9/2016 |

OTHER PUBLICATIONS

Japanese Office Action, dated Dec. 1, 2020, for corresponding Japanese Application No. 2018-074188, with an English machine translation.

Office Action dated Jul. 14, 2020 in Japanese Patent Application No. 2018-074188, with English translation.

* cited by examiner

AUTOMATIC LAYOUT APPARATUS, AUTOMATIC LAYOUT METHOD, AND AUTOMATIC LAYOUT PROGRAM

CROSS-REFERENCE TO RELATED APPLICATION

This application claims the benefit of priority to U.S. Provisional Application No. 62/483,492, filed on Apr. 10, 2017, which is incorporated by reference in its entirety.

BACKGROUND

Field of the Invention

The present invention relates to a display protocol for assisting image interpretation, and more particularly, an automatic layout apparatus, an automatic layout method, and an automatic layout program for automatically laying out images.

Related Art

In recent years, with the spread of medical information systems, a wide-area electronic medical record allowing the exchange of data between medical institutions for the purpose of cooperation in disease diagnosis and sharing of medical information in the community has been realized. As elemental technologies of the wide-area electronic medical record system, there is a picture archiving and communication system (PACS) provided in each medical institution. In the PACS, storage, viewing, and management of image data received from image capturing apparatuses (modalities), such as computed radiography (CR) apparatuses, computed tomography (CT) apparatuses, and magnetic resonance imaging (MRI) apparatuses, are performed. In addition, by managing image data using a digital imaging and communication in medicine (DICOM) standard, unified management of various types of image data has become possible.

In the image examination, a plurality of images (a simple X-ray image, a CT image, an MRI image, an ultrasound image, and the like) are captured for one patient, the captured images are read out from the PACS, and the read images are displayed on the screen of an interpretation viewer or the like so as to be able to be checked. In this case, images are displayed side by side for easy interpretation according to the purpose of examination. For example, a captured image before contrast and a captured image after contrast are displayed side by side. At the time of actual interpretation, images are manually arranged for each examination in many cases. Accordingly, selecting an image while watching the thumbnail image and designating a place where the image is to be displayed are repeated.

Therefore, the interpretation viewer has a function of automating this. As a specific method of automation, for example, a method of arranging images in the imaging order and a method of arranging images according to a rule defined based on information (DICOM tag information or the like) attached to the images are known. For example, JP2007-260061A discloses a method in which definition information, which defines the arrangement order of a plurality of medical images using supplementary information of the medical images, is used and the medical images are displayed so as to be arranged at positions defined according to the definition information using the supplementary information of the medical images in the case of simultaneously displaying the plurality of medical images on the screen. JP2013-106951A discloses a method of improving a layout matching the user's preference using a machine learning algorithm based on a workflow input by a user and providing a layout candidate applicable as a display protocol.

In order to quickly determine an examination image, performing image display according to the radiologist's preference is important in improving interpretation efficiency. In addition, once the arrangement of images is set in the display protocol according to the radiologist's preference, it is desirable that images are automatically displayed with the same display protocol for similar cases thereafter.

In addition, in a case where a medical information system in which a plurality of medical institutions cooperate with each other, such as a wide-area electronic medical record system, is constructed, a request for interpretation of an image captured in each medical institution is sent to a medical institution that has a radiologist specializing in interpretation. However, the description of supplementary information, such as the imaging order or the DICOM tag attached to the image, may not be standardized. Accordingly, in a case where the vendor (manufacturer) of an imaging apparatus or the imaging technician is different, images may be captured in different imaging order, or the method of describing tag information may be different. For this reason, there is a problem that the methods disclosed in JP2007-260061A and JP2013-106951A do not appropriately function.

SUMMARY

Therefore, in order to solve the aforementioned problem, it is an object of the invention to provide an automatic layout apparatus, an automatic layout method, and an automatic layout program for automatically laying out images with a display protocol optimal for interpretation.

An automatic layout apparatus of the invention comprises: reception means for receiving examination data including a plurality of examination images; storage means for storing layout information indicating a layout in which a size and an arrangement position of each image in a case of arranging a plurality of sample images on a screen are set; association means for associating the examination image similar to each sample image included in the layout with the sample image using a similarity between each sample image included in the layout and each of the plurality of examination images included in the examination data; and display means for displaying the examination image associated with the sample image at an arrangement position where the sample image associated with the examination image is arranged according to the layout information.

An automatic layout method of the invention is an automatic layout method in an automatic layout apparatus comprising storage means for storing layout information indicating a layout in which a size and an arrangement position of each image in a case of arranging a plurality of sample images on a screen are set, reception means, association means, and display means, and comprises: a step in which the reception means receives examination data including a plurality of examination images; a step in which the association means associates the examination image similar to each sample image included in the layout with the sample image using a similarity between each sample image included in the layout and each of the plurality of examination images included in the examination data; and a step in which the display means displays the examination image associated with the sample image at an arrangement position where the sample image associated with the examination image is arranged according to the layout information.

An automatic layout program of the invention causes a computer to function as: reception means for receiving examination data including a plurality of examination images; storage means for storing layout information indicating a layout in which a size and an arrangement position of each image in a case of arranging a plurality of sample images on a screen are set; association means for associating the examination image similar to each sample image included in the layout with the sample image using a similarity between each sample image included in the layout and each of the plurality of examination images included in the examination data; and display means for displaying the examination image associated with the sample image at an arrangement position where the sample image associated with the examination image is arranged according to the layout information.

"Layout information" refers to information including a screen division method and image arrangement positions at the time of arranging images on the screen. The screen division method includes, for example, a method of dividing the screen into two regions, four regions, or the like and the size of each divided region. "Examination data" refers to data necessary for diagnosing a disease, and includes a plurality of examination images. The examination images include still images and motion pictures captured by various modalities. The examination image may be an image obtained by converting document data regarding the examination.

It is preferable that the association means comprises: similarity acquisition means for acquiring a similarity between the examination image and the sample image for each combination of one of the sample images included in the layout and one of the examination images included in the examination data; and adjustment value acquisition means for acquiring an adjustment value of the similarity based on a relationship between imaging times of a sample image included in a first combination of two combinations and a sample image included in a second combination and a relationship between imaging times of an examination image included in the first combination and an examination image included in the second combination. Preferably, in a case where the sample image and the examination image are associated with each other so as to satisfy conditions in which the number of examination images associated with each of the sample images is one or less and the number of sample images associated with each of the examination images is one or less, the association means associates the sample image with the examination image using all the similarities acquired by the similarity acquisition means for the combination of the sample image and the examination image associated with each other and all the adjustment values acquired by the adjustment value acquisition means for the two combinations.

The similarity acquisition means may acquire the similarity based on a histogram of image data of the examination image and image data of the sample image.

It is preferable that, in a case where an order of imaging times of a sample image included in the first combination and a sample image included in the second combination is the same as an order of imaging times of an examination image included in the first combination and an examination image included in the second combination, the adjustment value acquisition means sets the adjustment value to a value that makes the similarity higher than in a case where the order of imaging times of the sample image included in the first combination and the sample image included in the second combination is not the same as the order of imaging times of the examination image included in the first combination and the examination image included in the second combination.

It is preferable that the association means determines the examination image, which is to be associated with the sample image by a graph matching method, using a weighted sum of all the similarities acquired from the combination and all the adjustment values acquired from the two combinations in a case of associating the examination image with the sample image so as to satisfy the conditions.

In a case where a tomographic image is included in a sample image of the layout and a tomographic image is included in an examination image of the examination data, it is preferable that the association means associates an examination image whose tomographic image has the same cross-sectional direction as a tomographic image of the sample image, among a plurality of examination images included in the examination data, with the sample image.

In a case where a tomographic image is included in a sample image of the layout and a tomographic image is included in an examination image of the examination data, it is preferable that the association means comprises: similarity acquisition means for acquiring a similarity between the examination image and the sample image for each combination of one of the sample images included in the layout and one of the examination images included in the examination data; and adjustment value acquisition means for acquiring an adjustment value of the similarity based on a relationship between tomographic positions of a sample image included in a first combination of two combinations and a sample image included in a second combination and a relationship between tomographic positions of an examination image included in the first combination and an examination image included in the second combination. In a case where the sample image and the examination image are associated with each other so as to satisfy conditions in which the number of examination images associated with each of the sample images is one or less and the number of sample images associated with each of the examination images is one or less, it is preferable that the association means associates the sample image with the examination image using all the similarities acquired by the similarity acquisition means for the combination of the sample image and the examination image associated with each other and all the adjustment values acquired by the adjustment value acquisition means for the two combinations.

It is preferable that, in a case where an order of tomographic positions of a sample image included in the first combination and a sample image included in the second combination is the same as an order of tomographic positions of an examination image included in the first combination and an examination image included in the second combination, the adjustment value acquisition means sets the adjustment value to a value that makes the similarity higher than in a case where the order of tomographic positions of the sample image included in the first combination and the sample image included in the second combination is not the same as the order of tomographic positions of the examination image included in the first combination and the examination image included in the second combination.

According to the invention, an examination image similar to each sample image included in the layout is associated with the sample image using the similarity between each sample image included in the layout and each of a plurality of examination images included in examination data, and the examination image associated with the sample image is displayed at the arrangement position where the sample image associated with the examination image is arranged according to the layout information. Therefore, since examination images having a different imaging order or a different tag information description method according to the vendor of an imaging apparatus or the imaging technician at the appropriate position of the prepared layout, it is possible to improve working efficiency.

DETAILED DESCRIPTION

Figure 1:
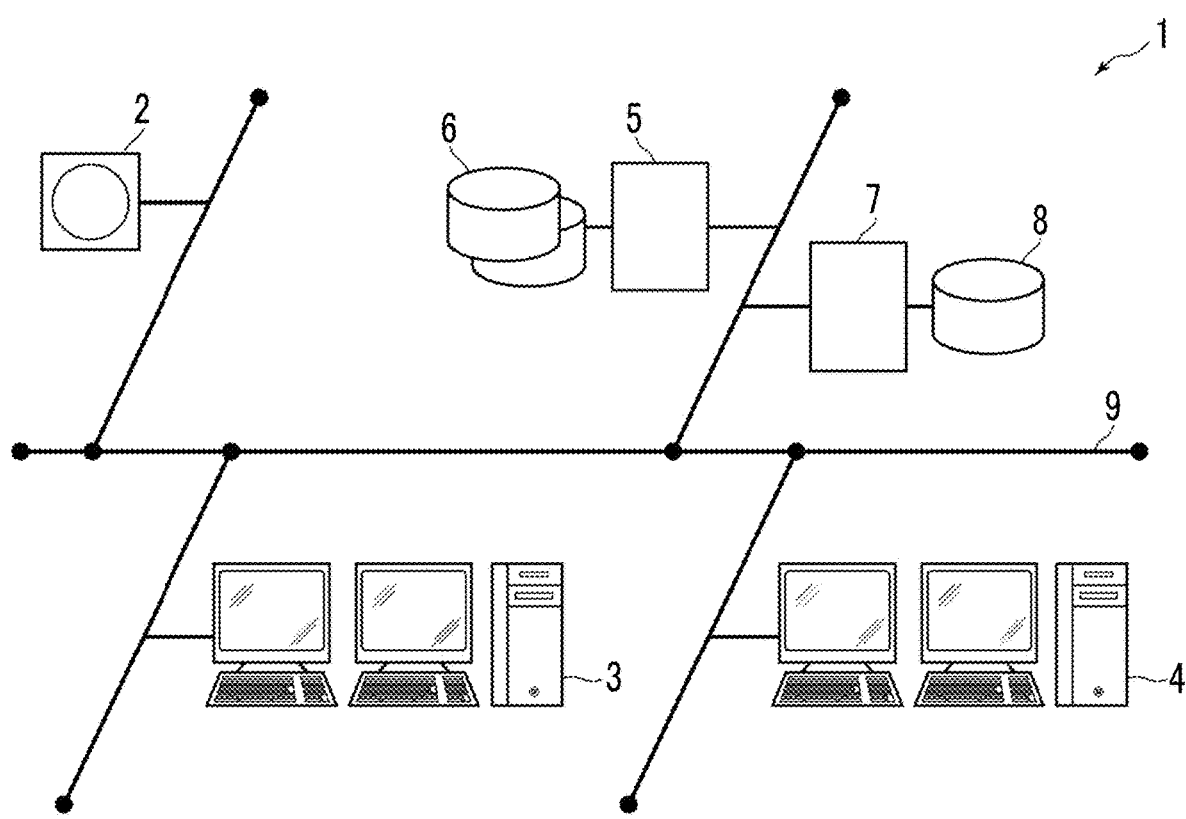
FIG. 1 is a diagram showing the schematic configuration of a medical information system in which an automatic layout apparatus according to an embodiment of the invention is introduced.

FIG. 1 shows the schematic configuration of a medical information system 1 in which an automatic layout apparatus according to an embodiment of the invention is introduced. The medical information system 1 is a system for performing imaging of an examination target part of a subject and storage of the obtained image, interpretation of an image captured by a radiologist in a radiology department and creation of an interpretation report, and viewing of an interpretation report by a doctor in a medical department of a requester and detailed observation of an image to be interpreted, based on an examination order from a doctor of a medical department using a known ordering system. As shown in FIG. 1, the medical information system 1 is configured to include a modality 2, a workstation for radiologists 3, a medical department workstation 4, an image management server 5, an image database 6, an interpretation report server 7, and an interpretation report database 8 that are communicably connected to each other through a network 9. An application program for causing each apparatus to function as a component of the medical information system 1 is installed. The application program may be installed from a recording medium, such as a CD-ROM, or may be installed after being downloaded from a storage device of a server connected through a network, such as the Internet.

The modality 2 includes an apparatus that generates an examination image showing an examination target part of a subject by imaging the examination target part of the subject, adds supplementary information specified by the DICOM standard to the examination image, and outputs the examination image. As specific examples, a CT apparatus, an MRI apparatus, a positron emission tomography (PET) apparatus, an ultrasound apparatus, and a CR apparatus using a planar X-ray detector (flat panel detector; FPD) can be mentioned.

The workstation for radiologists 3 is a computer used by a radiologist in the radiology department for image interpretation and creation of an interpretation report, and has a known hardware configuration, such as a central processing unit (CPU), a main storage device, an auxiliary storage device, an input and output interface, a communication interface, an input device, a display device, and a data bus. A known operating system or the like is installed on the workstation for radiologists 3, and one or a plurality of high-definition displays are provided as a display device. In the workstation for radiologists 3, each process, such as an image transmission request to the image management server 5, display of an image received from the image management server 5, automatic detection and highlighting of a lesion-like portion in an image, and creation and display of an interpretation report, is performed by executing a software program for each process. In addition, the workstation for radiologists 3 transmits the created interpretation report to the interpretation report server 7 through the network 9, and makes a request for registration of the interpretation report in the interpretation report database 8.

The medical department workstation 4 is a computer used by a doctor in the medical department for detailed observation of images or viewing of interpretation reports and for viewing and inputting of electronic medical records, and has a known hardware configuration, such as a CPU, a main storage device, an auxiliary storage device, an input and output interface, a communication interface, an input device, a display device, and a data bus. A known operating system or the like is installed on the medical department workstation 4, and one or a plurality of high-definition displays are provided as a display device. In the medical department workstation 4, each process, such as an image viewing request to the image management server 5, display of an image received from the image management server 5, automatic detection or highlighting of a lesion-like portion in an image, an interpretation report viewing request to the interpretation report server 7, and display of an interpretation report received from the interpretation report server 7, is performed by executing a software program for each process. In addition, the medical department workstation 4 transmits a motion picture in an endoscopic examination or the like performed in each medical department to the image management server 5 through the network 9, and makes a request for registration of the motion picture in the image database 6.

The image management server 5 has a software program for providing a function of a data base management system (DBMS) to a general-purpose computer. The image management server 5 includes a large capacity storage in which the image database 6 is formed. This storage may be a large capacity hard disk device connected to the image management server 5 through a data bus, or may be a disk device connected to a storage area network (SAN) or a network attached storage (NAS) connected to the network 9.

In the image database 6, examination images obtained by imaging a plurality of patients with the modality 2 and supplementary information are registered. The supplementary information includes, for example, an image identification (ID) for identifying each image, a patient ID for identifying a subject, an examination ID for identifying an examination, a unique identification (UID) allocated for each medical image, examination date and examination time at which the medical image is generated, the type of a modality used in an examination for acquiring the medical image, patient information such as patient's name, age, and gender, an examination part (imaging part), imaging conditions (whether or not a contrast medium is used, radiation dose, and the like), and information such as a series number in a case where a plurality of tomographic images are acquired in one examination.

In a case where a viewing request from the workstation for radiologists 3 is received through the network 9, the image management server 5 searches for the examination image registered in the image database 6 and transmits the extracted examination image to the workstation for radiologists 3 that is an examination image request source.

The interpretation report server 7 has a software program for providing a function of a data base management system (DBMS) to a general-purpose computer. In a case where an interpretation report registration request from the workstation for radiologists 3 is received, the interpretation report server 7 arranges the interpretation report in a database format and registers the interpretation report in the interpretation report database 8.

In the interpretation report database 8, information including, for example, an image ID for identifying an interpretation target image or a representative image, a radiologist ID for identifying an image diagnostician who performed the interpretation, position information of a region of interest, findings, and certainty of findings is registered.

The network 9 is a local area network that connects various apparatuses in a hospital. In a case where the workstation for radiologists 3 is installed in another hospital or clinic, the network 9 may be configured to connect local area networks of respective hospitals through the Internet or a dedicated circuit. In any case, the network 9 is preferably a network capable of realizing high-speed transfer of medical images, such as an optical network.

Figure 13:
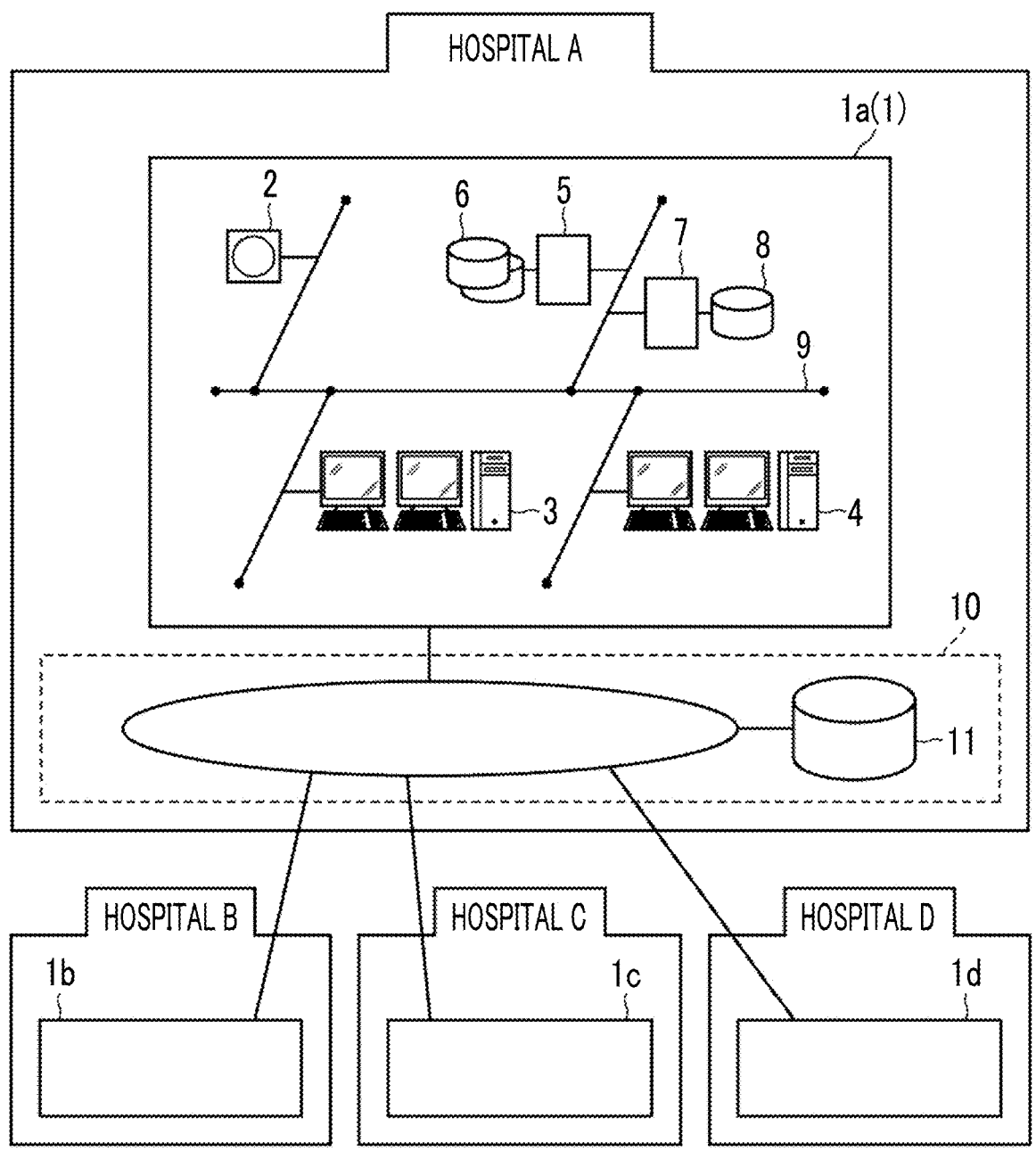
FIG. 13 is a diagram showing a schematic configuration in which an archive system is connected to a medical information system.

As shown in FIG. 13, an archive system 10 may be connected to the medical information system 1. The archive system 10 includes a large-capacity storage device 11 for storing and managing not only medical images or various motion pictures of medical information systems 1*a* to 1*d* in a plurality of medical institutions but also a wide range of clinical information, such as an examination request document (examination order) describing the examination purpose and the like handled by each medical department in the medical institution and a document obtained by converting other kinds of examination information, such as a blood test result, as a document.

In a case where a user, such as an image diagnostician, performs an operation of making a request for interpretation and viewing of the observation target image, the workstation for radiologists 3 transmits a viewing request to the image management server 5 and acquires a required image. Then, the image is displayed on a display. The workstation for radiologists 3 has a function of the automatic layout apparatus of the invention, and this processing is realized by executing the installed application program.

Figure 2:
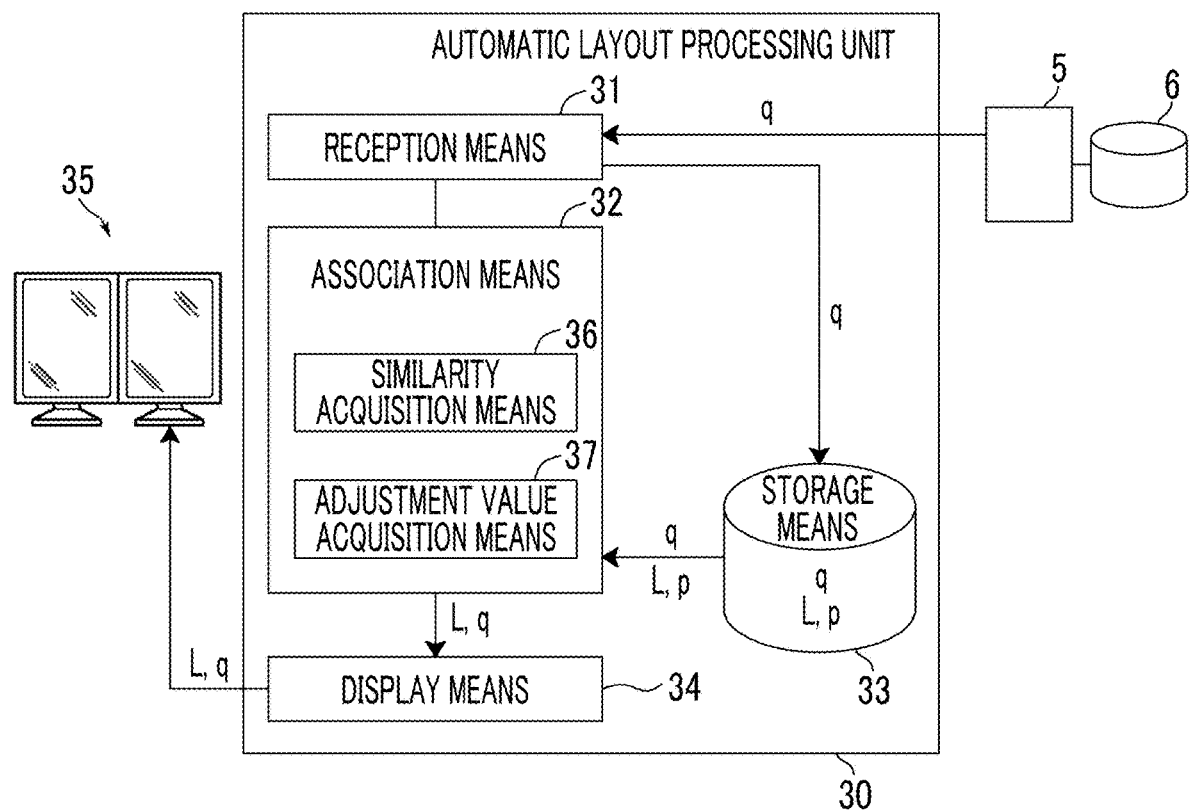
FIG. 2 is a functional block diagram of the automatic layout apparatus of the invention.

FIG. 2 is a block diagram schematically showing the configuration of the automatic layout apparatus according to the embodiment of the invention, which is mounted in the workstation for radiologists 3, and the flow of data. The automatic layout apparatus of the invention will be described below as an automatic layout processing unit of the workstation for radiologists 3. As shown in FIG. 2, an automatic layout processing unit 30 of the invention is configured to include reception means 31, association means 32, storage means 33, and display means 34. One or a plurality of displays 35 are connected to the display means 34.

In the workstation for radiologists 3, in a case where the patient ID of an examination target is input by the user, such as a radiologist, the patient ID of the examination target and an image transmission request are transmitted from the workstation for radiologists 3 to the image management server 5, and the reception means 31 receives a plurality of examination images q searched for from the image database 6 as examination data. The received examination images q are temporarily stored in the storage means 33. The examination images q include images obtained by imaging using various modalities 2. Simple X-ray images, a current image and a past image obtained by imaging the same part, images before and after administration of a contrast medium, a plurality of tomographic images (such as CT images or MRI images), images captured under different imaging conditions (such as T1 weighting and T2 weighting of MRI images), motion pictures captured by an endoscope, and the like are included in the examination images q. In addition, an electronic document obtained by converting an examination request or examination information from the archive system 10 as a document may be received, and those obtained by converting the electronic document into image data (for example, a PDF file) may be included in the examination image.

The storage means 33 stores a plurality of sample images p and layout information L showing a layout in which the sample images p are arranged on the screen. The sample image p is an image serving as a sample in the case of arranging examination images on the screen, and is an image serving as a reference in the case of arranging examination images. In the layout information L, information regarding a screen division method at the time of arranging images on the screen and arrangement position information regarding which sample image p is to be arranged in each of the divided regions are defined. The information of the screen division method also includes the size of each of the divided display regions. For example, information for vertically dividing the screen into two left and right regions so as to have the same size, information for vertically and horizontally dividing the screen into four regions so as to have the same size, or information for displaying the main image on the left half of the screen so as to be large and displaying the remaining images vertically on the right half is defined.

The layout may be a single screen or a plurality of screens. For example, the layout may be configured to include a plurality of pages, and a screen division method and the arrangement position of each sample image p in the case of displaying a plurality of pages in which the sample image p is arranged on the display screen while switching the plurality of pages may be defined as the layout information L. Alternatively, the layout information L may define a screen division method of each of screens of a plurality of displays and the arrangement position of each sample image p in a case where the plurality of displays are connected to the workstation for radiologists 3. For example, on a single display, a combination of a screen division method of a certain page and the sample image p arranged in each divided region and a screen division method of the next page and the sample image p arranged in each divided region may be one piece of layout information L. In addition, on a plurality of displays, information indicating that the screen is divided into four regions in a display A and which sample image p is to be arranged in each divided region and indicating that the screen is divided into two regions in a display B and which sample image p is to be arranged in each divided region may be one piece of layout information L. In addition, information of a screen division method in the case of displaying display screens of a plurality of pages on a plurality of displays while switching the display screens and the sample image p arranged on each divided region may be one piece of layout information L.

In the storage means 33, the standard sample image p, a standard image division method, and the layout information L in which the standard arrangement position of the sample image p is defined may be prepared in advance and stored. Alternatively, in a case where the radiologist performs interpretation in the workstation for radiologists 3, information obtained by recording a screen division method and image arrangement positions in a case where the images read out from the image database 6 are arranged on the screen of the display may be the layout information L, and the images arranged at that time may be stored as the sample images p. In addition, the examination images q may be displayed using the layout information L stored in the storage means 33, and the layout information L and the sample images p may be updated according to the layout in a case where the image arrangement positions or the screen division method is changed according to the radiologist's preference.

Figure 3A:
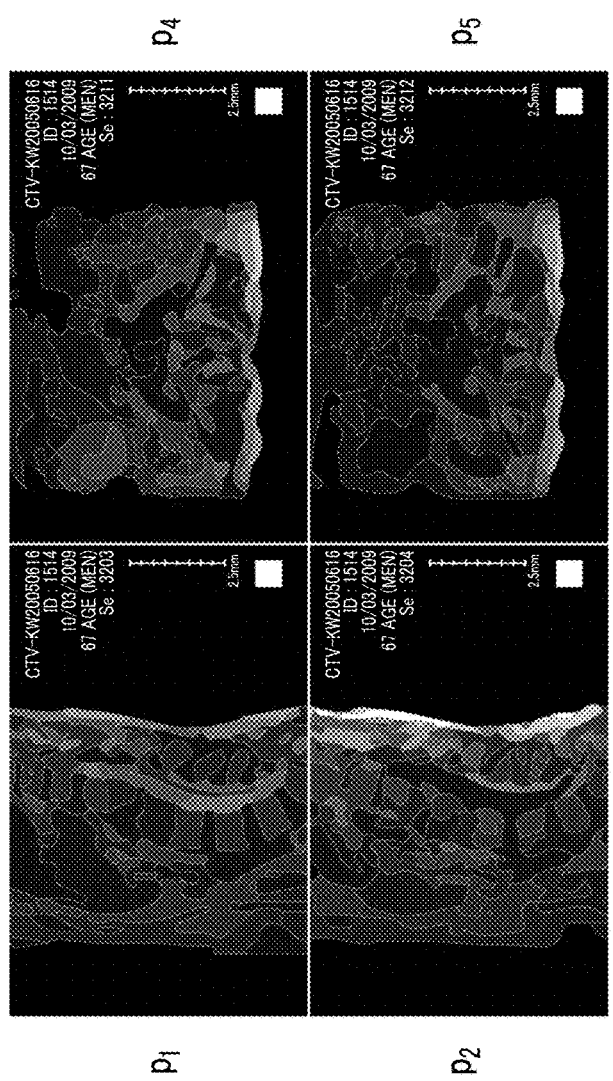
FIGS. 3A and 3B are diagrams showing examples of a layout in which sample images are arranged.
Figure 3B:
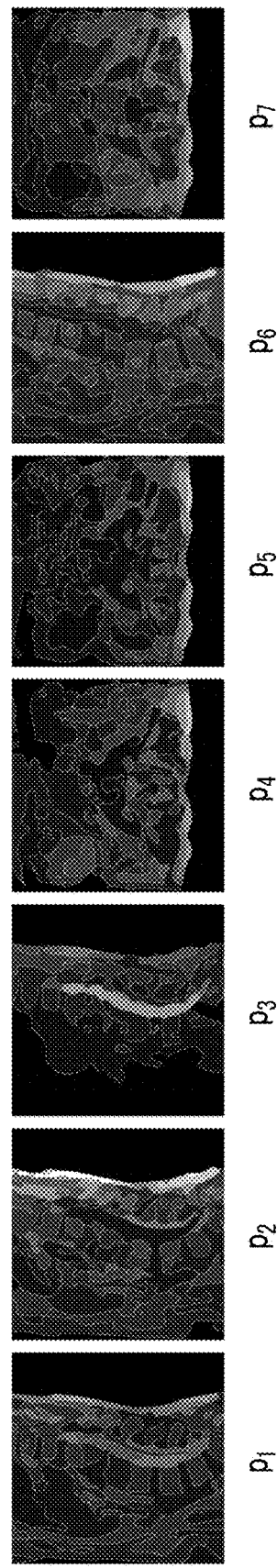

FIG. 3A shows an example of a layout in which the sample images p are arranged according to the layout information L. FIG. 3B shows sample images $p_1$ to $p_7$ arranged in respective regions of the layout. In FIG. 3A, the screen is divided into four regions, the sample image $p_1$ is arranged in the upper left region, a sample image $p_2$ is arranged in the lower left region, the sample image $p_4$ is arranged in the upper right region, and the sample image $p_5$ is arranged in the lower right region. In FIG. 3A, the sample images $p_3$, $p_6$, and $p_7$ are not displayed on the screen, but the sample images $p_3$, $p_6$, and $p_7$ may be arranged on the next page.

Such layout information L may be transmitted from the workstation for radiologists 3 to the image management server 5 and stored in the image database 6 so as to be associated with the sample images p. In a case where an operation for interpretation is performed in the workstation for radiologists 3, the image management server 5 may be requested to transmit the layout information L and the sample images p, and the transmitted layout information L and sample images p may be stored in the storage means 33. It is preferable that a plurality of types of combinations of the sample images p and the layout information L are stored in advance in the storage means 33 so that selection from the plurality of types of layout information L according to a case or radiologist's preference is possible.

The association means 32 includes similarity acquisition means 36 and adjustment value acquisition means 37, and selects the examination images q similar to the sample images p forming the layout from examination data and associates the examination images q with the sample images p. In the case of associating the sample images p and the examination images q with each other, two or more examination images q are not associated with one sample image p. In a case where the number of examination images q included in the examination data is smaller than the number of sample images p arranged in the layout, there may be no examination image q associated with the sample image p. In addition, the same examination image q is not associated with two or more sample images p. That is, the number of examination images q associated with the sample image p is one or less, and the number of sample images p associated with the examination image q included in the examination data is also one or less.

The similarity acquisition means 36 calculates a similarity for each combination of one of the sample images p included in the layout and one of the examination images q included in the examination data. As the similarity, a similarity between the pixel data of the sample image p and the examination image q is calculated. Pixel data refers to a group of pixels forming an image. Specifically, the similarity can be acquired using cross-correlation, histogram intersection, and the like. The pixel data of an image will be described below so as to be distinguished from supplementary information of an image, such as a DICOM tag, a file name, and imaging date and time.

However, the similarity between pixel data may be high even between the sample image p and the examination image q in different cross-sectional directions, such as an axial cross-section and a sagittal cross-section. A cross-sectional direction is determined with reference to supplementary information, such as a DICOM tag, and a similarity is calculated so as to increase in a case where the cross-sectional directions of a tomographic image included in the sample image p of the layout and a tomographic image included in the examination image q of the examination data are the same and decrease in a case where the cross-sectional directions are not the same.

In two combinations, the adjustment value acquisition means 37 calculates an adjustment value of the similarity based on the relationship between the sample image p included in a first combination a and the sample image p included in a second combination b and the relationship between the examination image q included in the first combination a and the examination image q included in the second combination b. In the case of images before and after administration of a contrast medium that are obtained by imaging the same part, the similarity between images before the administration and the similarity between images after the administration should be high even between the sample image p and the examination image q. However, there is a possibility that the similarity between the sample image p before the administration and the examination image q after the administration will become high depending on how the image contrast medium is diffused. It may be difficult to determine corresponding images only with the similarity of pixel data, such as a plurality of images having different cardiac beat phases of the heart. Therefore, in a case where the relationship between the imaging times of the two sample images p included in the combinations a and b is the same as the relationship between the imaging times of the two examination images q included in the combinations a and b, the adjustment value is set to a value such that the similarity is higher than that in a case where the relationship between the imaging times of the two sample images p included in the combinations a and b is not the same as the relationship between the imaging times of the two examination images q included in the combinations a and b.

Alternatively, in a case where a plurality of tomographic images are included in the sample images p and the examination images q, the arrangement order of the tomographic images is not changed. For example, in the case of an axial image, in a case where the relationship between the tomographic positions of the two sample images p, which are included in the combinations a and b, in the body axis direction is the same as the relationship between the tomographic positions of the two examination images q included in the combinations a and b, the adjustment value is set to a value such that the similarity is higher than that in a case where the relationship between the tomographic positions of the two sample images p is not the same as the relationship between the tomographic positions of the two examination images q.

Figure 4:
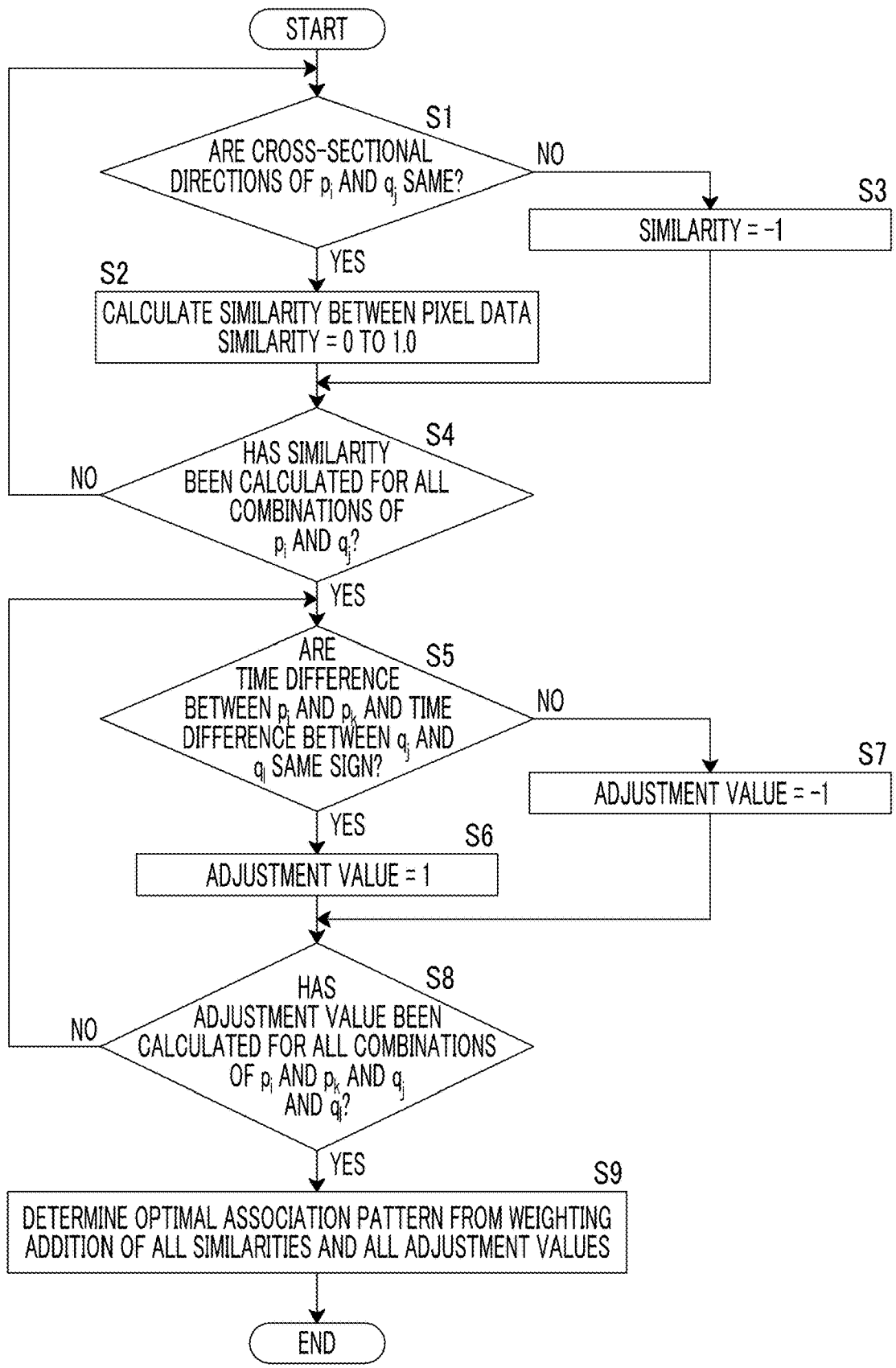
FIG. 4 is a flowchart of a process for associating a sample image and an examination image with each other.
Figure 5:
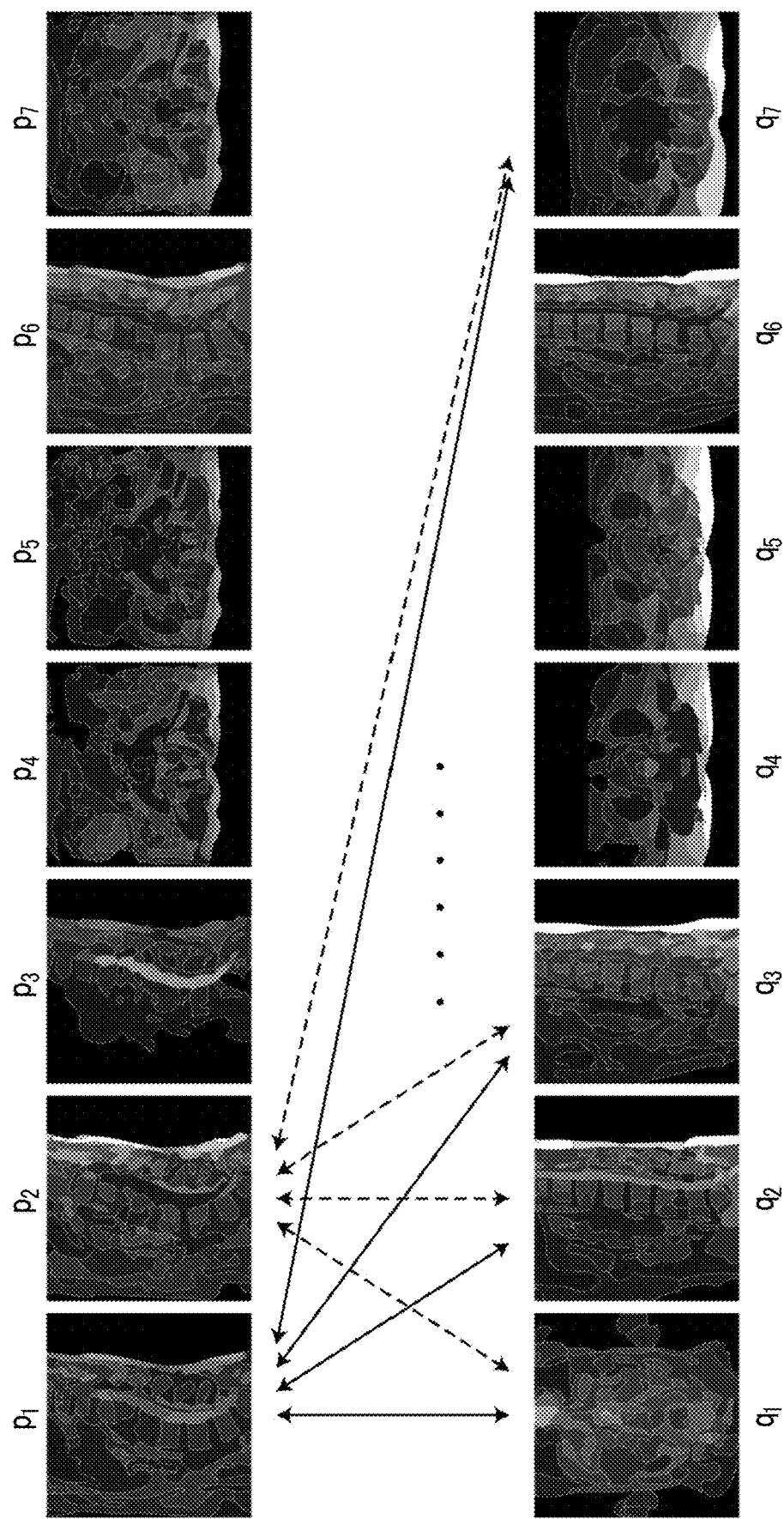
FIG. 5 is a diagram showing examples of a sample image and an examination image.

A process in which the sample image p and the examination image q are associated with each other using the similarity and the adjustment value will be specifically described with reference to the flowchart of FIG. 4. FIG. 5 shows examples of sample images $p_1$ to $p_7$ and examination images $q_1$ to $q_7$.

First, a set of sample images p included in the layout is assumed to be P, and a set of examination images q included in the examination data is assumed to be Q. The similarity acquisition means 36 calculates a similarity between a sample image $p_i$ that is an element of P and an examination image $q_j$ that is an element of Q using a histogram intersection. As shown in FIG. 5, a similarity is calculated for all combinations of the sample images $p_1$ to $p_7$ and the examination images $q_1$ to $q_7$. That is, a similarity between $p_1$ and each of $q_1, q_2, q_3, \ldots, q_7$ is calculated, and a similarity between $p_2$ and each of $q_1, q_2, q_3, \ldots, q_7$ is calculated. Similarly, a similarity between each of $p_3$ to $p_7$ and each of $q_1, q_2, q_3, \ldots, q_7$ is calculated.

The cross-sectional directions of the sample image $p_i$ and the examination image $q_j$ can be determined based on the description of "Image Orientation" of the DICOM tag, for example. For example, in a case where the sample image $p_i$ is an axial cross-section perpendicular to the body axis, "first row" and "first column" of "Image Orientation" almost match (1, 0, 0) and (0, 1, 0), respectively. Therefore, the degree of matching between two vectors obtained by referring to "Image Orientation" of the examination image $q_j$ and the two vectors (1, 0, 0) and (0, 1, 0) of the sample image $p_i$ is calculated using an inner product operation. In a case where the cross-sectional directions of the sample image $p_i$ and the examination image $q_j$ are the same (S1—Yes), the similarity between pixel data is calculated as a similarity $\theta_a$ using a histogram intersection (S2).

Figure 6:
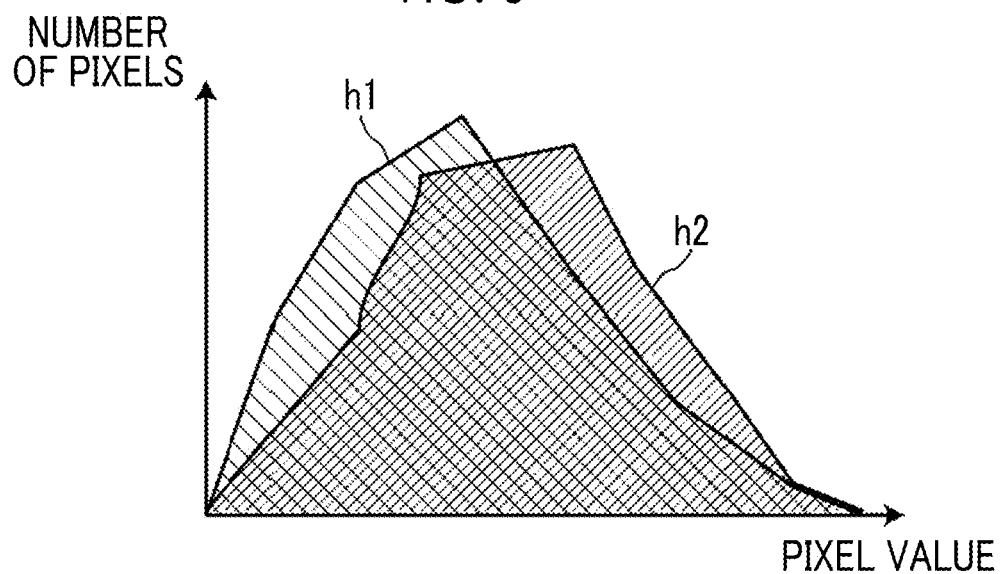
FIG. 6 is a diagram illustrating a method of calculating a similarity from histogram intersection.
Figure 7:
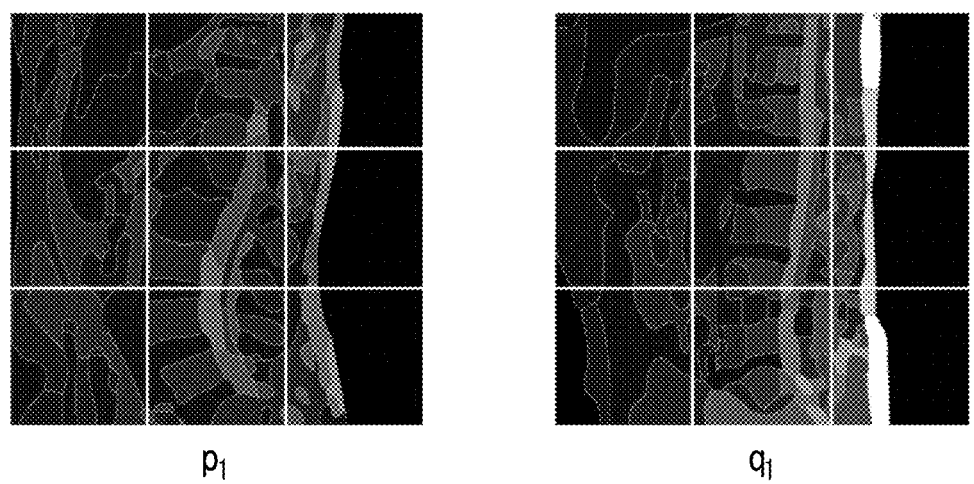
FIG. 7 is a diagram illustrating a method of calculating a similarity reflecting the composition of a screen.

As shown in FIG. 6, the histogram intersection refers to a ratio of the intersection between a histogram h1 of the sample image $p_i$ and a histogram h2 of the examination image $q_j$. In this case, the similarity $\theta_a$ is a value of 0 to 1.0. In order to reflect the rough composition of the screen, for example, each of the sample image $p_i$ and the examination image $q_j$ may be equally divided into three regions vertically and horizontally (refer to FIG. 7), a histogram intersection may be calculated in each divided section of 3×3 sections (=nine sections), and the average value may be set as the similarity $\theta_a$ (S1—No). On the other hand, in a case where the cross-sectional directions of the sample image $p_i$ and the examination image $q_j$ are different, the similarity $\theta_a$ is set to −1 (S3). This is calculated for all combinations of $p_i$ and $q_j$ (S4).

Then, the adjustment value acquisition means 37 calculates an adjustment value $\theta_{ab}$ of the similarity in a case where the sample image $p_i$ and the examination image $q_j$ are associated with each other. The sample image $p_i$ and the examination image $q_j$ are associated with each other such that the number of examination images $q_j$ associated with the sample image $p_i$ is one or less and the number of sample images $p_i$ associated with the examination image $q_j$ included in the examination data is also one or less. Which association among all association patterns in the case of performing association so as to satisfy such association conditions is optimal is adjusted by using not only the similarity $\theta_a$ between the pixel data of the sample image $p_i$ and the pixel data of the examination image $q_j$ but also the adjustment value based on the relationship between the imaging times.

In a case where the examination image $q_j$ is associated with the sample image $p_i$ and the examination image $q_1$ is associated with the sample image $p_k$ between the set P and the set Q, the adjustment value $\theta_{ab}$ is calculated from the combination a of the sample image $p_i$ and the examination image $q_j$ and the combination b of the sample image $p_k$ and the examination image $q_1$. In a case where the sign of a difference $(T_a=t(p_k)-t(p_i))$ between the imaging time $t(p_i)$ of the sample image $p_i$ and the imaging time $t(p_k)$ of the sample image $p_k$ is the same as the sign of a difference $(T_b=t(q_1)-t(q_j))$ between the imaging time $t(q_j)$ of the examination image $q_j$ and the imaging time $t(q_1)$ of the examination image $q_1$ (S5—Yes), the adjustment value $\theta_{ab}$ is set to 1 (S6). In a case where the sign of the difference $T_a$ and the sign of the difference $T_b$ are not the same (S5—No), the adjustment value $\theta_{ab}$ is set to −1 (S7). This is calculated for all the two combinations a and b in each association pattern (S8).

Figure 8A:
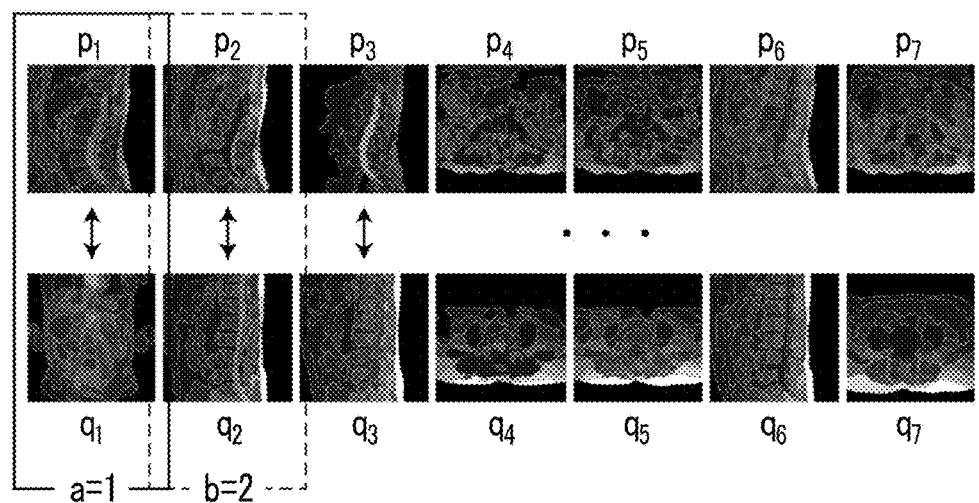
FIGS. 8A to 8C are diagrams illustrating a method of calculating an adjustment value.
Figure 8B:
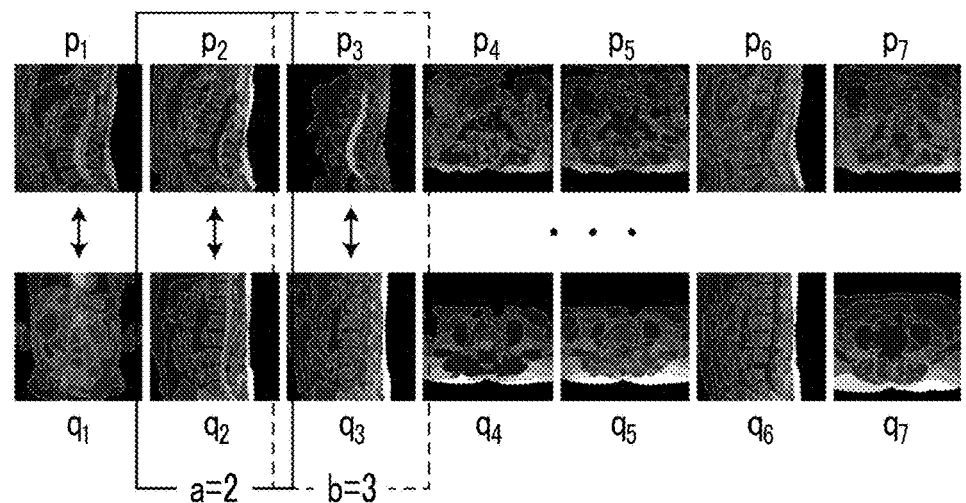
Figure 8C:
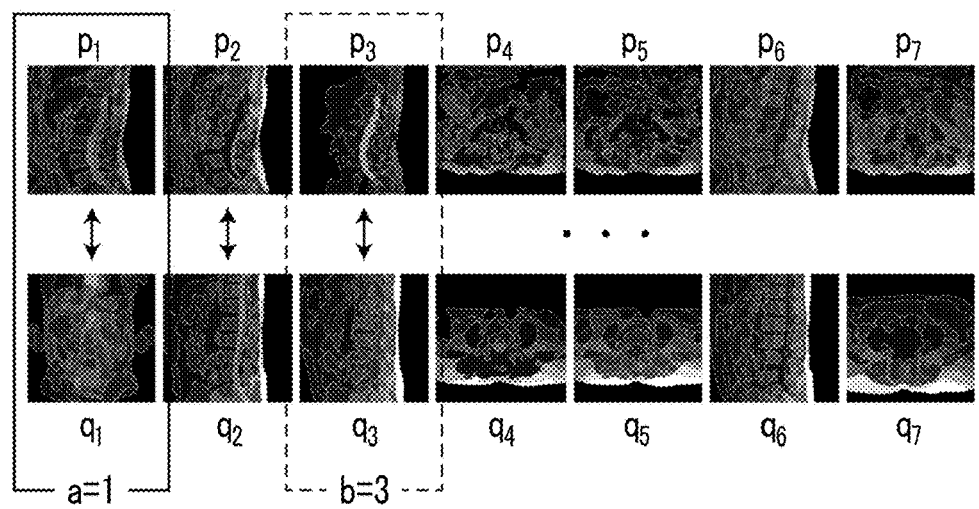

For example, as shown in FIGS. 8A and 8B, in the case of associating $p_1$ and $q_1$, $p_2$ and $q_2$, $p_3$ and $q_3$, ..., in a case where the difference between the imaging times of $p_1$ and $p_2$ and the difference between the imaging times of $q_1$ and $q_2$ are the same in the combination 1 of $p_1$ and $q_1$ and the combination 2 of $p_2$ and q2 (FIG. 8A), the adjustment value $\theta_{a=1, b=2}$ is set to 1. In the combination 2 of $p_2$ and $q_2$ and the combination 3 of $p_3$ and $q_3$ (FIG. 8B), in a case where the difference between the imaging times of $p_2$ and $p_3$ and the difference between the imaging times of $q_2$ and $q_3$ are not the same, the adjustment value $\theta_{a=2, b=3}$ is set to −1. In the combination 1 of $p_1$ and $q_1$ and the combination 3 of $p_3$ and $q_3$ (FIG. 8C), in a case where the difference between the imaging times of $p_1$ and $p_3$ and the difference between the imaging times of $q_1$ and $q_3$ are the same, the adjustment value $\theta_{a=1, b=3}$ is set to 1. In this manner, the adjustment value $\theta_{ab}$ is calculated for all the two combinations a and b.

Figure 9:
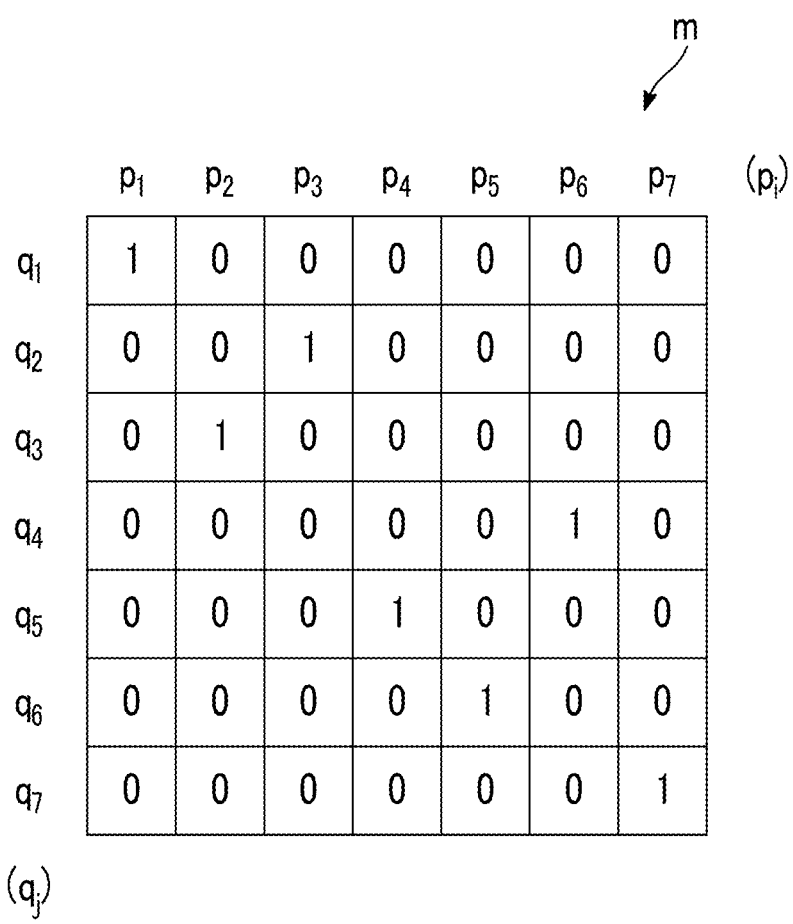
FIG. 9 is a diagram illustrating association between a set of sample images and a set of examination images.

As shown in FIG. 9, between the set P and the set Q, association between the sample image $p_i$ and the examination image $q_j$ is expressed with an association matrix m of elements of P×Q using binary data x of 0 and 1. In the association matrix m, the row indicates the sample image $p_i$ and the column indicates the examination image $q_j$. An element $x_{ij}$ in the i-th row and the j-th column indicates whether or not to associate the sample image $p_i$ with the examination image $q_j$. The element $x_{ij}$ in the i-th row and the j-th column is set to 0 in a case where the sample image $p_i$ is associated with the examination image $q_j$, and is set to 1 in a case where the sample image $p_i$ is not associated with the examination image $q_j$. In this case, in the set P and the set Q, all association patterns that associate the sample image $p_i$ and the examination image $q_j$ with each other are created so as to satisfy the conditions in which at most one examination image $q_j$ is associated with the sample image $p_i$ and at most one sample image $p_i$ is associated with the examination image $q_j$. A set M of association patterns expressed by the association matrix m can be expressed by the following Equation (1).

$$M = \left\{ x \in \{0, 1\}^{P \times Q} \,\middle|\, \sum_{p \in P} x_{pq} \leq 1, \sum_{q \in Q} x_{pq} \leq 1 \right\} \quad (1)$$

In all the patterns that associate the sample image $p_i$ and the examination image $q_j$ included in the set M with each other, optimal association between the sample image $p_i$ and the examination image $q_j$ is determined by determining a pattern having the highest similarity between the sample image $p_i$ of the set P and the examination image $q_j$ of the set Q (S9). This can be replaced with a problem of maximizing the following Equation (2) in which the similarity $\theta_a$ calculated by the similarity acquisition means 36 and the adjustment value $\theta_{ab}$ calculated by the adjustment value acquisition means 37 are weighted and added. For example, this problem can be solved using the graph matching method described in the document "L. Torresani, V. Kolmogorov, and C. Rother: "Feature correspondence via graph matching: Models and global optimization", ECCV 2008". In the following Equation (2), the first term means that all of the similarities $\theta_a$ of the combination of the sample image $p_i$ and the examination image $q_j$ at which $x_{ij}=1$ are added, and the second term means that all the adjustment values $\theta_{ab}$ obtained from the relationship between the two combinations (combination a and combination b) of the sample image $p_i$ and the examination image $q_j$ at which $x_{ij}=1$ in the association matrix m of FIG. 8 are weighted and added. It is preferable that the coefficient K is an empirically optimal value.

$$\max_{x \in M} E(x \mid \theta) = \sum_{a \in A} \theta_a x_a + k \sum_{(a,b) \in N} \theta_{ab} x_a x_b \quad (2)$$

Here, A indicates a set of combinations of the sample image $p_i$ and the examination image $q_j$. N indicates a set of the combination a of the sample image $p_i$ and the examination image $q_j$ and the combination b of the sample image $p_k$ and the examination image $q_l$. k indicates a coefficient for determining the load of similarity and adjustment value. $x_a$ indicates a value of the element $x_{ij}$ corresponding to the combination $a(p_i, q_j)$ in binary data x. $x_b$ indicates a value of an element $x_{kl}$ corresponding to the combination $b(p_k, q_l)$ in binary data x.

The display means 34 divides the screen using an image division method according to the layout information L, and displays the examination image q associated with the sample image p at the arrangement position (region) where the sample image p is arranged in each of the divided regions according to the association result of the association means 32.

Figure 10:
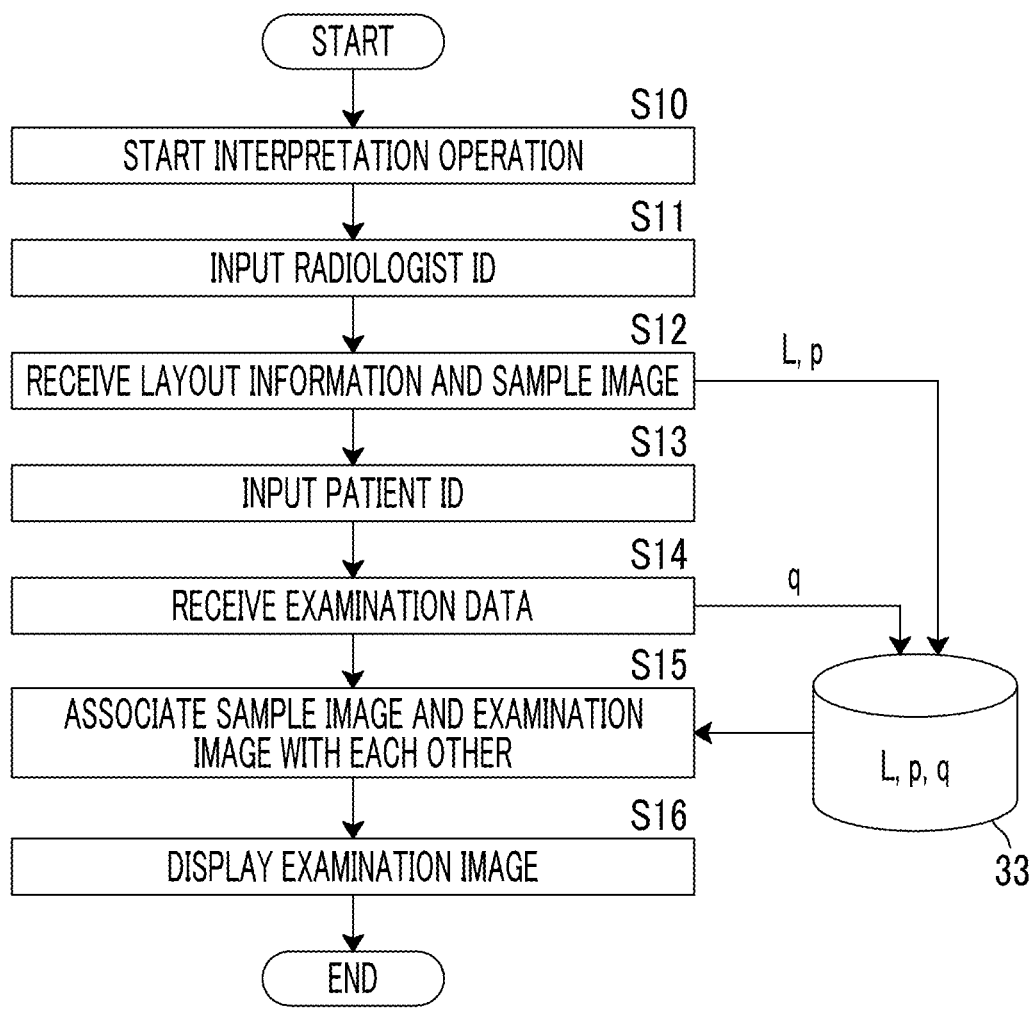
FIG. 10 is a flowchart illustrating the operation of the automatic layout apparatus.

Next, the operation of the automatic layout apparatus of the present embodiment will be described with reference to the flowchart of FIG. 10.

In a case where a radiologist performs an operation for interpretation in the workstation for radiologists 3 (S10), an input radiologist ID is transmitted from the workstation for radiologists 3 to the image management server 5 (S11), and the layout information L and the sample image p corresponding to the radiologist ID are transmitted from the image database 6 and stored in the storage means 33 (S12).

Then, in a case where the radiologist inputs a patient ID of an examination target (S13), the reception means 31 of the workstation for radiologists 3 transmits the patient ID and a request for the transmission of the examination image q to the image management server 5. The image management server 5 searches for the examination image q, to which the patient ID is assigned, from the image database 6 and transmits the examination image q to the workstation for radiologists 3. The reception means 31 stores the received examination image q in the storage means 33 as examination data (S14).

Using the association means 32 described in detail above, a set of a plurality of association patterns in which the sample image p and the examination image q used in the layout information L stored in the storage means 33 are associated with each other are created, and an association pattern having the highest similarity among the plurality of association patterns is determined (S15).

The display means 34 divides the screen of the display 35 according to the screen division method of the layout information L, and arranges and displays the examination image q in a region, in which the sample image p associated with each examination image q is arranged, according to the association between the sample image p and the examination image q determined by the association means 32 (S16).

Figure 11:
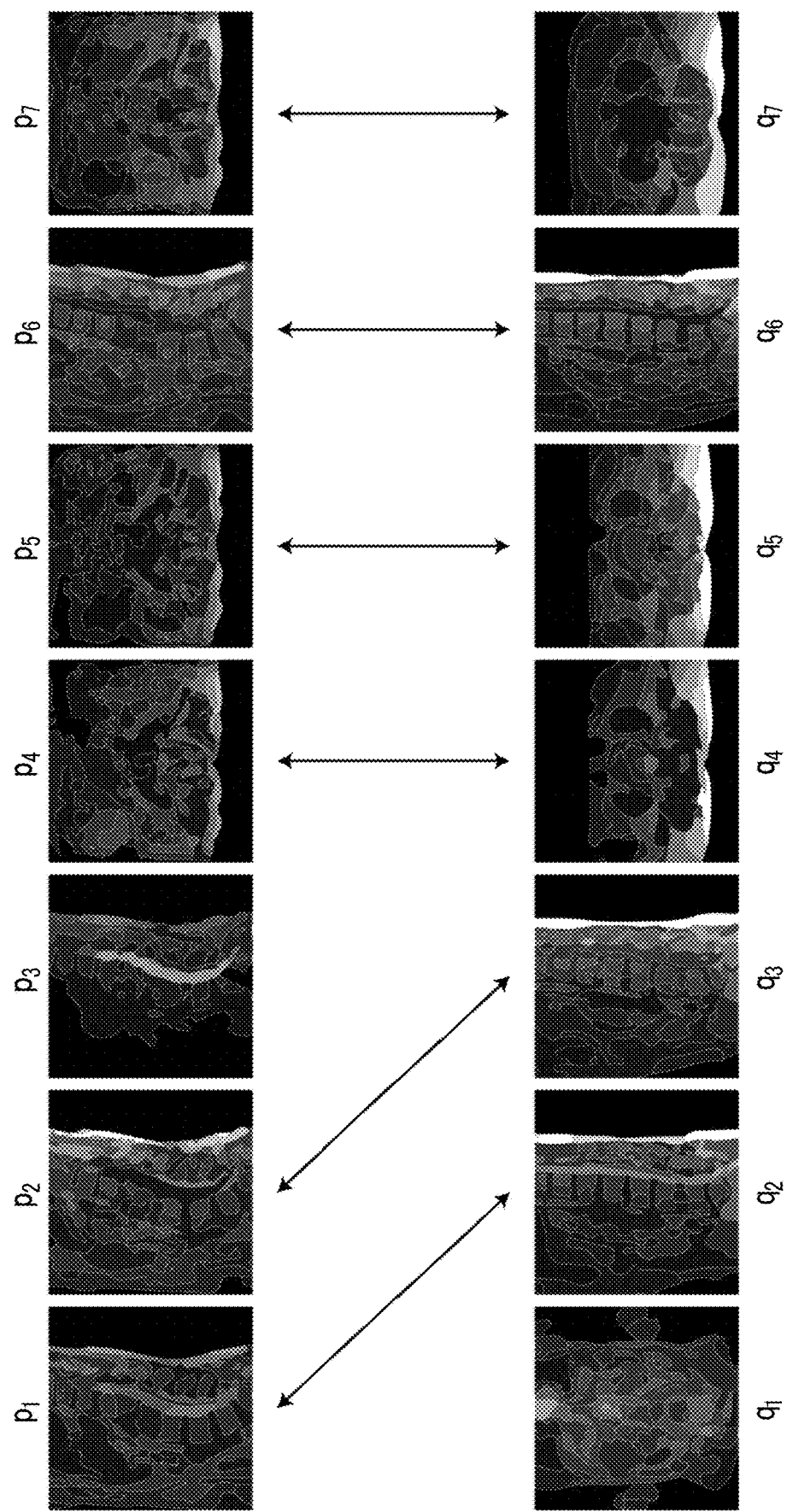
FIG. 11 is a diagram showing an example of an association result between sample images and examination images.
Figure 12:
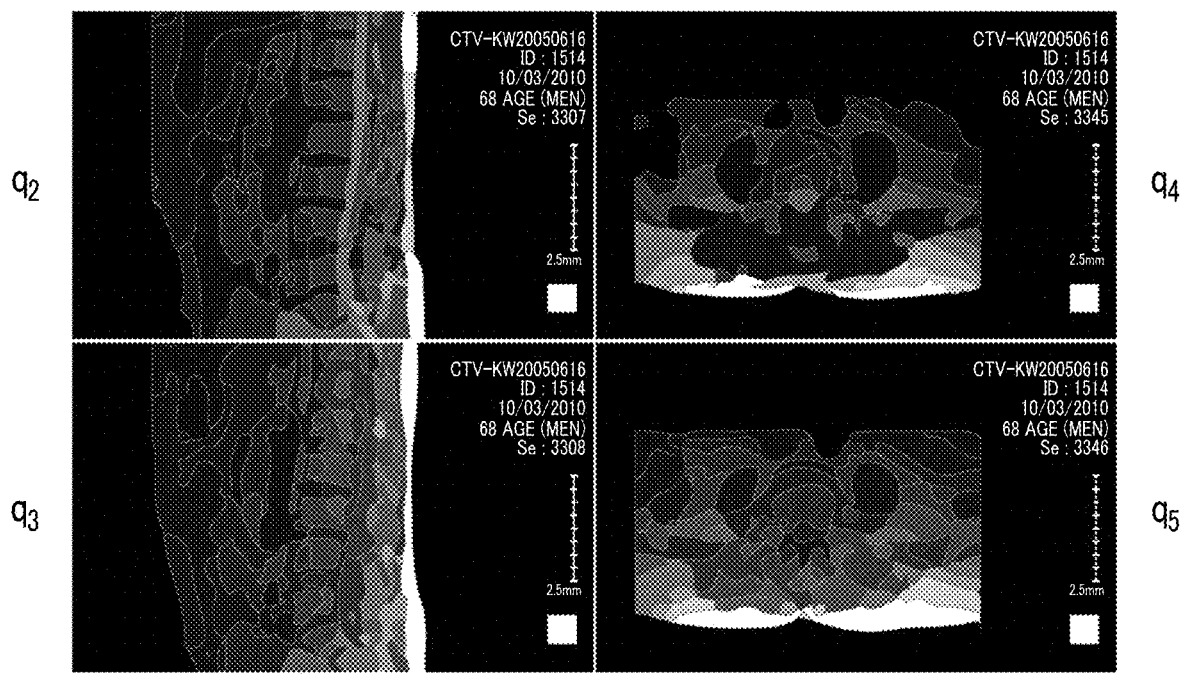
FIG. 12 is a diagram showing an example in which examination images are displayed on a display screen.

In a case where the sample images $p_1$ to $p_7$ and the examination images $q_1$ to $q_7$ in FIG. 5 are associated with each other by the association means 32 as shown in FIG. 11, images are displayed on the display screen as shown in FIG. 12 by the display means 34.

As described above, examination images similar to sample images arranged on the screen are arranged, and are arranged so that the order of imaging times of the sample images and the order of imaging times of the examination images are not reversed.

In the above description, the case where the association pattern is determined so that the order of the imaging times is the same between the sample image q and the examination image p has been described. However, in a case where a tomographic image is included in the sample image of the layout and a tomographic image is also included in the examination image of the examination data, it is also possible to determine the association pattern so that the order of the positional relationship of the tomographic images is the same between the sample image and the examination image.

In this case, the similarity acquisition means 36 calculates the similarity $\theta_a$ in the same manner as described above. However, in the case of calculating the adjustment value $\theta_{ab}$ from the combination a of the sample image $p_i$ and the examination image $q_j$ and the combination b of the sample image $p_k$ and the examination image $q_l$, in a case where the sign of a difference $D_1$ between the tomographic positions of the sample image $p_i$ and the sample image $p_k$ is the same as the sign of a difference $D_2$ between the tomographic positions of the examination image $q_j$ and the examination image $q_l$, the adjustment value acquisition means 37 sets the adjustment value $\theta_{ab}$ to 1. In a case where the sign of the difference $D_1$ and the sign of the difference $D_2$ are not the same, the adjustment value acquisition means 37 sets the adjustment value $\theta_{ab}$ to −1. By maximizing Equation (2) or (3) that adds the similarity $\theta_a$ and the adjustment value $\theta_{ab}$, it is possible to determine the optimal combination of the sample image $p_i$ and the examination image $q_j$.

In addition, arrangement can be done so that the positional relationship between the tomographic images of the sample images and the positional relationship between the tomographic images of the examination images do not contradict each other. As described in detail above, in the layout that could not be determined accurately from supplementary information of an image in the related art, it is possible to perform accurate association between a sample image and an examination image with reference to the sample image.

What is claimed is:

1. An automatic layout apparatus, comprising:
processing circuitry configured to receive examination data including a plurality of examination images;
a storage for storing layout information indicating a layout in which a size and an arrangement position of each of a plurality of sample images on a screen are set,
wherein the plurality of sample images are different from the plurality of examination images, the plurality of sample images defining a plurality of standard sample images to be arranged in one of a plurality of layouts,
wherein the processing circuitry is further configured to associate the examination image with the sample image using a similarity between each of the plurality of sample images included in the layout and each of the plurality of examination images included in the examination data, wherein the examination images are associated with the sample images according to an optimal pattern, the similarity being calculated between pixels forming the sample image and pixels forming the examination image, and
wherein the layout information is associated with the plurality of sample images and the association between the layout information and the plurality of sample images indicates how the associated plurality of examination images are to be displayed; and
a display for displaying the examination image associated with the sample image at an arrangement position where the sample image associated with the examination image is arranged according to the layout information,
wherein the processing circuitry is further configured to:
acquire the similarity between the examination image and the sample image for each of combinations of one of the sample images included in the layout and one of the examination images included in the examination data; and
in association patterns in which the sample images in the layout and the examination images of the examination data are associated with each other so as to satisfy conditions in which the number of the examination image associated with each of the sample images is one or less and the number of the sample image associated with each of the examination images is one or less, the processing circuitry is further configured to specify the optimal pattern from the association patterns using total similarities of the association patterns, the total similarities being obtained based on all the similarities that are acquired for all combinations of the sample image and the examination image associated with each other in each of the association patterns, the optimal pattern having the highest total similarity.

2. The automatic layout apparatus according to claim 1, wherein the processing circuitry is further configured to:
acquire an adjustment value of the similarity based on a relationship between imaging times of the sample image included in a first combination of the combinations and the sample image included in a second combination of the combinations, and a relationship between imaging times of the examination image included in the first combination and the examination image included in the second combination, and
the total similarities being all the similarities that are acquired for all combinations of the sample image and the examination image associated with each other and all the adjustment values that are acquired for all sets of the first and second combinations in each of the association patterns.

3. The automatic layout apparatus according to claim 2, wherein the processing circuitry is further configured to acquire the similarity based on a histogram of values of pixels forming the examination image and a histogram of values of pixels forming the sample image.

4. The automatic layout apparatus according to claim 2, wherein, in a case where an order of imaging times of the sample image included in the first combination and the sample image included in the second combination is the same as an order of imaging times of the examination image included in the first combination and the examination image included in the second combination, the processing circuitry is further configured to set the adjustment value to a value that makes the similarity higher than in a case where the order of imaging times of the sample image included in the first combination and the sample image included in the second combination is not the same as the order of imaging times of the examination image included in the first combination and the examination image included in the second combination.

5. The automatic layout apparatus according to claim 2, wherein the processing circuitry is further configured to determine the examination image, which is to be associated with the sample image by a graph matching method, using a weighted sum of all the similarities acquired from all combinations and all the adjustment values acquired from all sets of the first and second combinations in a case of associating the examination image with the sample image so as to satisfy the conditions.

6. The automatic layout apparatus according to claim 1, wherein a tomographic image is included in the sample images of the layout,
a tomographic image is included in the examination images of the examination data, and
the processing circuitry is further configured to associate the examination image whose tomographic image has the same cross-sectional direction as the tomographic image of the sample images, among the plurality of examination images included in the examination data, with the sample image.

7. The automatic layout apparatus according to claim 1, wherein a tomographic image is included in the sample images of the layout,
a tomographic image is included in the examination images of the examination data,
the processing circuitry is further configured to:
acquire an adjustment value of the similarity based on a relationship between tomographic positions of the sample image included in a first combination of the combinations and the sample image included in a second combination of the combinations, and a relationship between tomographic positions of the examination image included in the first combination and the examination image included in the second combination, and
the total similarities being all the similarities that are acquired for all combinations of the sample image and the examination image associated with each other and all the adjustment values that are acquired for all sets of the first and second combinations in each of the association patterns.

8. The automatic layout apparatus according to claim 7, wherein, in a case where an order of tomographic positions of the sample image included in the first combination and the sample image included in the second combination is the same as an order of tomographic positions of the examination image included in the first combination and the examination image included in the second combination, the processing circuitry is further configured to set the adjustment value to a value that makes the similarity higher than in a case where the order of tomographic positions of the sample image included in the first combination and the sample image included in the second combination is not the same as the order of tomographic positions of the examination image included in the first combination and the examination image included in the second combination.

9. An automatic layout method in an automatic layout apparatus comprising a storage for storing layout information indicating a layout in which a size and an arrangement position of each image in a case of arranging a plurality of sample images on a screen are set, processing circuitry, and a display, the method comprising:

receiving examination data including a plurality of examination images, the plurality of sample images being different from the plurality of examination images, the plurality of sample images defining a plurality of standard sample images to be arranged in one of a plurality of layouts;

associate the examination image with the sample image using a similarity between each of the plurality of sample images included in the layout and each of the plurality of examination images included in the examination data, wherein the examination images are associated with the sample images according to an optimal pattern, the similarity being calculated between pixels forming the sample image and pixels forming the examination image, and wherein the layout information is associated with the plurality of sample images and the association between the layout information and the plurality of sample images indicates how the associated plurality of examination images are to be displayed; and display the examination image associated with the sample image at an arrangement position where the sample image associated with the examination image is arranged according to the layout information, wherein the similarity between the examination image and the sample image for each of combinations of one of the sample images included in the layout and one of the examination images included in the examination data is acquired; and association patterns in which the sample images in the layout and the examination images of the examination data are associated with each other so as to satisfy conditions in which the number of the examination image associated with each of the sample images is one or less and the number of the sample image associated with each of the examination images is one or less, the processing circuitry is further configured to specify the optimal pattern from the association patterns using total similarities of the association patterns, the total similarities being obtained based on all the similarities that are acquired for all combinations of the sample image and the examination image associated with each other in each of the association patterns, the optimal pattern having the highest total similarity.

10. A non-transitory computer-readable storage medium storing therein an automatic layout program causing a computer to:

receive examination data including a plurality of examination images;

store layout information indicating a layout in which a size and an arrangement position of each of a plurality of sample images on a screen are determined, the plurality of sample images being different from the plurality of examination images, the plurality of sample images defining a plurality of standard sample images to be arranged in one of a plurality of layouts;

associate the examination image with the sample image using a similarity between each of the plurality of sample images included in the layout and each of the plurality of examination images included in the examination data, wherein the examination images are associated with the sample images according to an optimal pattern, the similarity being calculated between pixels forming the sample image and pixels forming the examination image, and wherein the layout information is associated with the plurality of sample images and the association between the layout information and the plurality of sample images indicates how the associated plurality of examination images are to be displayed; and display the examination image associated with the sample image at an arrangement position where the sample image associated with the examination image is arranged according to the layout information, wherein the similarity between the examination image and the sample image for each of combinations of one of the sample images included in the layout and one of the examination images included in the examination data is acquired; and association patterns in which the sample images in the layout and the examination images of the examination data are associated with each other so as to satisfy conditions in which the number of the examination image associated with each of the sample images is one or less and the number of the sample image associated with each of the examination images is one or less, the processing circuitry is further configured to specify the optimal pattern from the association patterns using total similarities of the association patterns, the total similarities being obtained based on all the similarities that are acquired for all combinations of the sample image and the examination image associated with each other in each of the association patterns, the optimal pattern having the highest total similarity.

* * * * *